(12) United States Patent
Milsom et al.

(10) Patent No.: US 9,320,587 B2
(45) Date of Patent: Apr. 26, 2016

(54) METHOD AND APPARATUS FOR ENDOSCOPICALLY TREATING RECTAL PROLAPSE

(75) Inventors: Jeffrey Milsom, New York, NY (US); Howard Riina, Scarsdale, NY (US); J. Frederick Cornhill, New York, NY (US)

(73) Assignee: Cornell University, Ithaca, NY (US)

( * ) Notice: Subject to any disclaimer, the term of this patent is extended or adjusted under 35 U.S.C. 154(b) by 299 days.

(21) Appl. No.: 13/641,422

(22) PCT Filed: Apr. 14, 2011

(86) PCT No.: PCT/US2011/032556
§ 371 (c)(1),
(2), (4) Date: Dec. 31, 2012

(87) PCT Pub. No.: WO2011/130556
PCT Pub. Date: Oct. 20, 2011

(65) Prior Publication Data
US 2013/0102841 A1    Apr. 25, 2013

Related U.S. Application Data

(63) Continuation-in-part of application No. 12/263,774, filed on Nov. 3, 2008, now Pat. No. 8,430,890.

(60) Provisional application No. 61/324,178, filed on Apr. 14, 2010, provisional application No. 60/985,009, filed on Nov. 2, 2007.

(51) Int. Cl.
| A61F 2/00 | (2006.01) |
| A61F 13/00 | (2006.01) |
| A61B 1/31 | (2006.01) |

(Continued)

(52) U.S. Cl.
CPC ............... *A61F 2/0022* (2013.01); *A61B 1/31* (2013.01); *A61B 17/0401* (2013.01); *A61B 1/0014* (2013.01); *A61B 17/0218* (2013.01);
(Continued)

(58) Field of Classification Search
CPC ............ A61B 1/0014; A61B 17/0218; A61B 17/0401; A61B 17/0487; A61B 2017/00818; A61B 2017/0225; A61B 2017/0417; A61B 2017/0419; A61B 2017/0488; A61B 2017/0496; A61B 2017/06052; A61B 2017/22067; A61B 2017/22069; A61B 1/31; A61F 2/0022
USPC ................. 600/37, 29–31, 101; 128/897–899
See application file for complete search history.

(56) References Cited

U.S. PATENT DOCUMENTS

| 5,323,790 A | 6/1994 | Guhle et al. |
| 5,458,608 A | 10/1995 | Wortrich |

(Continued)

FOREIGN PATENT DOCUMENTS

WO    WO 2005/000111    1/2005

*Primary Examiner* — Navin Natnithithadha
*Assistant Examiner* — Sunita Reddy
(74) *Attorney, Agent, or Firm* — Pandiscio & Pandiscio

(57) ABSTRACT

A method for treating rectal prolapse, the method comprising: inserting a rectum-gripping and advancement apparatus into a prolapsed rectum via the anus; maneuvering the rectum-gripping and advancement apparatus so that the rectum-gripping and advancement apparatus securely engages the rectum; advancing the rectum-gripping and advancement apparatus distally so as to return the prolapsed rectum to its normal, non-prolapsed state; and securing the rectum to supporting tissue whereby to retain the rectum in its normal, non-prolapsed state.

21 Claims, 25 Drawing Sheets

(51) Int. Cl.
*A61B 17/04* (2006.01)
*A61B 1/00* (2006.01)
*A61B 17/02* (2006.01)
*A61B 17/00* (2006.01)
*A61B 17/06* (2006.01)
*A61B 17/22* (2006.01)

(52) U.S. Cl.
CPC ... *A61B17/0487* (2013.01); *A61B 2017/00818* (2013.01); *A61B 2017/0225* (2013.01); *A61B 2017/0417* (2013.01); *A61B 2017/0419* (2013.01); *A61B 2017/0488* (2013.01); *A61B 2017/0496* (2013.01); *A61B 2017/06052* (2013.01); *A61B 2017/22067* (2013.01); *A61B 2017/22069* (2013.01)

(56) References Cited

U.S. PATENT DOCUMENTS

| | | | |
|---|---|---|---|
| 6,036,641 | A | 3/2000 | Taylor et al. |
| 6,626,916 | B1* | 9/2003 | Yeung et al. .................. 606/139 |
| 2003/0208100 | A1 | 11/2003 | Levy |
| 2004/0106943 | A1* | 6/2004 | Cappiello et al. ............. 606/192 |
| 2005/0119524 | A1* | 6/2005 | Sekine et al. ................. 600/114 |
| 2006/0030884 | A1 | 2/2006 | Yeung et al. |
| 2007/0066869 | A1* | 3/2007 | Hoffman ....................... 600/121 |
| 2008/0015614 | A1* | 1/2008 | Kaleta et al. .................. 606/144 |
| 2008/0103361 | A1 | 5/2008 | Makower et al. |
| 2008/0228030 | A1* | 9/2008 | Godin ............................ 600/106 |
| 2009/0156996 | A1 | 6/2009 | Milsom et al. |

* cited by examiner

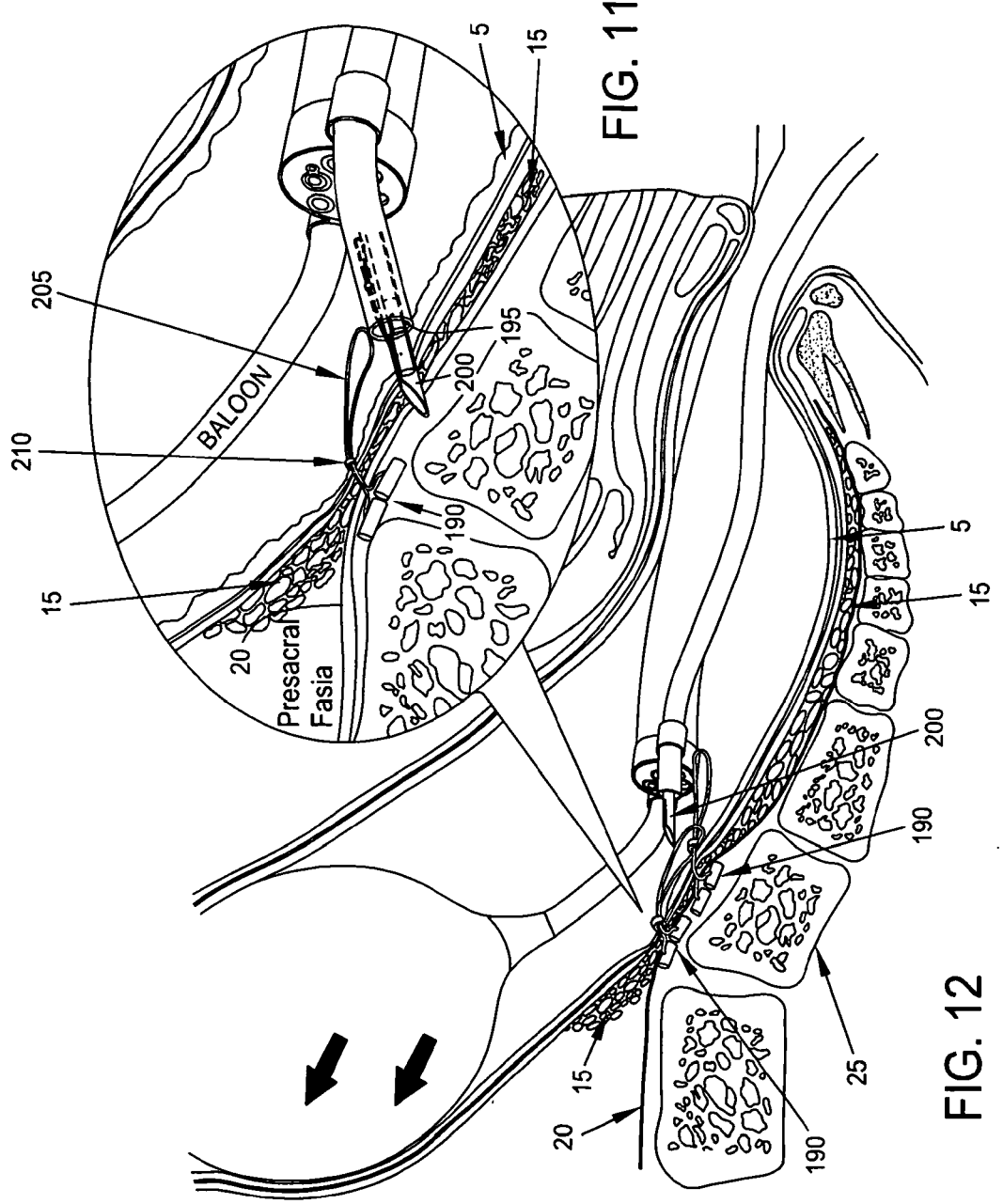

METHOD AND APPARATUS FOR ENDOSCOPICALLY TREATING RECTAL PROLAPSE

REFERENCE TO PENDING PRIOR PATENT APPLICATIONS

This patent application:

(i) is a continuation-in-part of prior U.S. patent application Ser. No. 12/263,774, filed Nov. 3, 2008 by Jeffrey Milsom et al. for METHOD AND APPARATUS FOR ENDOSCOPICALLY TREATING RECTAL PROLAPSE, which in turn claims benefit of prior U.S. Provisional Patent Application Ser. No. 60/985,009, filed Nov. 2, 2007 by Jeffrey Milsom et al. for ENDOSCOPIC RECTOPEXY; and (ii) claims benefit of prior U.S. Provisional Patent Application Ser. No. 61/324,178, filed Apr. 14, 2010 by Jeffrey Milsom et al. for METHOD AND APPARATUS FOR ENDOSCOPICALLY TREATING RECTAL PROLAPSE).

The three (3) above-identified patent applications are hereby incorporated herein by reference.

FIELD OF THE INVENTION

This invention relates to surgical methods and apparatus in general, and more particularly to surgical methods and apparatus for treating rectal prolapse.

BACKGROUND OF THE INVENTION

Rectal prolapse is a medical condition in which the walls of the rectum are not properly held in place, so that the rectum prolapses towards the anus and, in many cases, through the anal sphincter and outside the body.

There are three primary conditions which fall under the general category of rectal prolapse: (i) where the entire rectum protrudes through the anus (i.e., so-called "full thickness rectal prolapse"); (ii) where only the rectal mucosa prolapses (i.e., so-called "mucosal prolapse"); and (iii) where the rectum may collapse but not protrude through the anus (i.e., so-called "internal intussusception"). Rectal prolapse may be caused by a variety of conditions, e.g., advanced age, long term straining during defecation, pregnancy and childbirth, etc., and is typically characterized by a progression of symptoms, e.g., prolapse during bowel movements, prolapse during muscular stress (e.g., sneezing), prolapse during routine activities (e.g., walking) and, finally, chronic prolapse in which the rectum ceases to retract.

Mild cases of rectal prolapse can sometimes be treated secondarily, i.e., by reducing rectal straining through dietetic or pharmaceutical approaches. However, more severe cases of rectal prolapse must generally be treated surgically, either through abdominal surgery or perineal surgery. In any case, such surgery is substantial and traumatic in nature.

Thus there is a need for a new and improved approach for treating rectal prolapse, wherein the surgery is performed endoscopically so as to minimize trauma for the patient.

SUMMARY OF THE INVENTION

This and other objects of the present invention are addressed by the provision and use of a new and improved approach for treating rectal prolapse, wherein the surgery is performed endoscopically so as to minimize trauma for the patient.

In one form of the invention, there is provided a method for treating rectal prolapse, the method comprising:

inserting an expandable element into a prolapsed rectum via the anus;

expanding the expandable element so that the expandable element securely engages the rectum;

advancing the expanded element distally so as to return the prolapsed rectum to its normal, non-prolapsed state; and securing the rectum to supporting tissue whereby to retain the rectum in its normal, non-prolapsed state.

In another form of the invention, there is provided an endoscope assembly for treating rectal prolapse, the endoscope assembly comprising:

an endoscope;

a balloon catheter; and a fastener deployment device;

wherein the endoscope, balloon catheter and fastener deployment device are mounted together for insertion as a unit.

In another form of the invention, there is provided an endoscope assembly for treating rectal prolapse, the endoscope assembly comprising:

an endoscope;

a rectum-gripping and advancing mechanism; and a fastener deployment device;

wherein the endoscope, the rectum-gripping and advancing mechanism, and the fastener deployment device are mounted together for insertion as a unit;

and further wherein the rectum gripping and advancing mechanism is selected from the group consisting of a balloon catheter, expandable arms, and an expandable frame.

In another form of the invention, there is provided a method for treating rectal prolapse, the method comprising:

inserting a rectum-gripping and advancement apparatus into a prolapsed rectum via the anus;

maneuvering the rectum-gripping and advancement apparatus so that the rectum-gripping and advancement apparatus securely engages the rectum;

advancing the rectum-gripping and advancement apparatus distally so as to return the prolapsed rectum to its normal, non-prolapsed state; and securing the rectum to supporting tissue whereby to retain the rectum in its normal, non-prolapsed state.

In another form of the invention, there is provided a rectum-gripping and advancement apparatus for treating rectal prolapse comprising:

a shaft having a distal end and a proximal end; and a tissue support for engaging the interior wall of a rectum and repositioning the interior wall of the rectum.

In another form of the invention, there is provided an assembly for treating rectal prolapse, the assembly comprising:

an endoscope;

a rectum-gripping and advancement apparatus for treating rectal prolapse comprising:

a shaft having a distal end and a proximal end; and a tissue support for engaging the interior wall of a rectum and repositioning the interior wall of the rectum; and a fastener deployment device.

BRIEF DESCRIPTION OF THE DRAWINGS

These and other objects and features of the present invention will be more fully disclosed in, or rendered obvious by, the following detailed description of the preferred embodiments of the invention, which is to be considered together with the accompanying drawings wherein like numbers refer to like parts and further wherein:

FIGS. 10-12 are schematic views showing the fastener deployment device of the novel endoscope assembly securing the rectum to supporting tissue;

DETAILED DESCRIPTION OF THE OF THE PREFERRED EMBODIMENTS OF THE INVENTION

Figure 1:
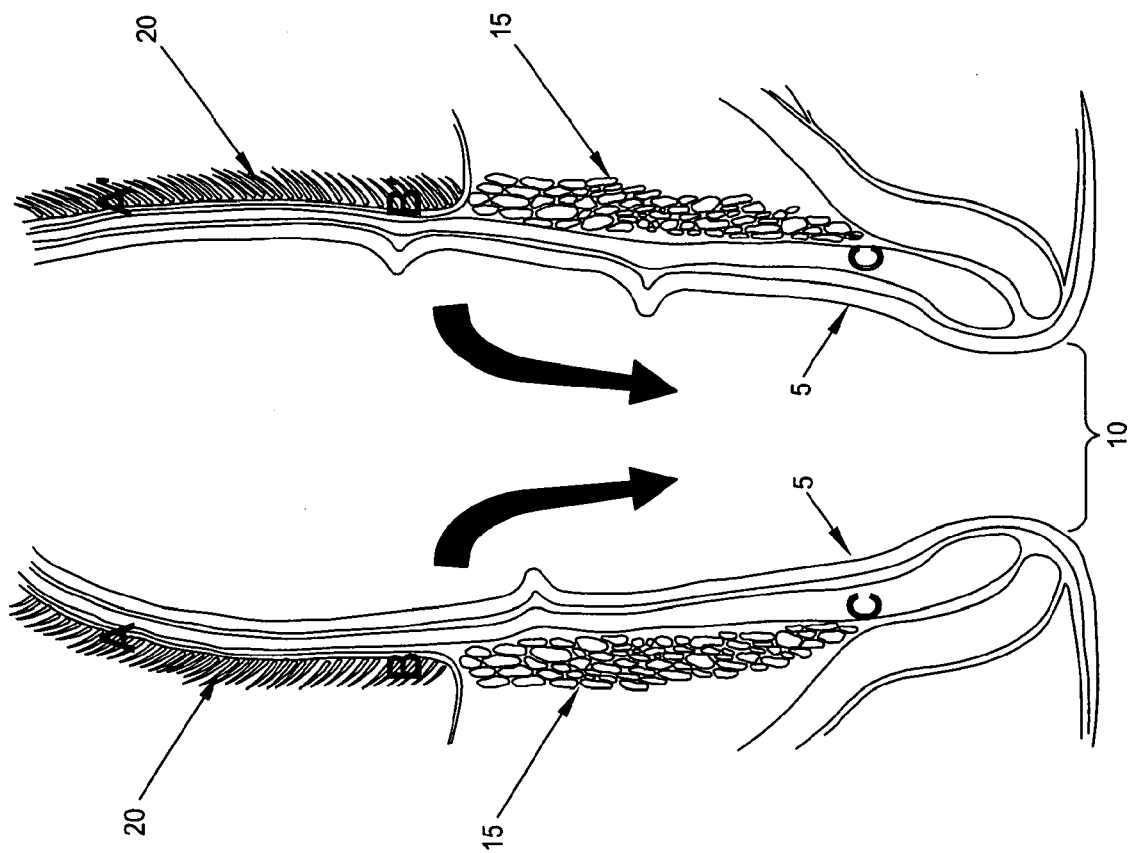
FIG. 1 is a schematic view of normal rectal anatomy, as seen in coronal view.
Figure 2:
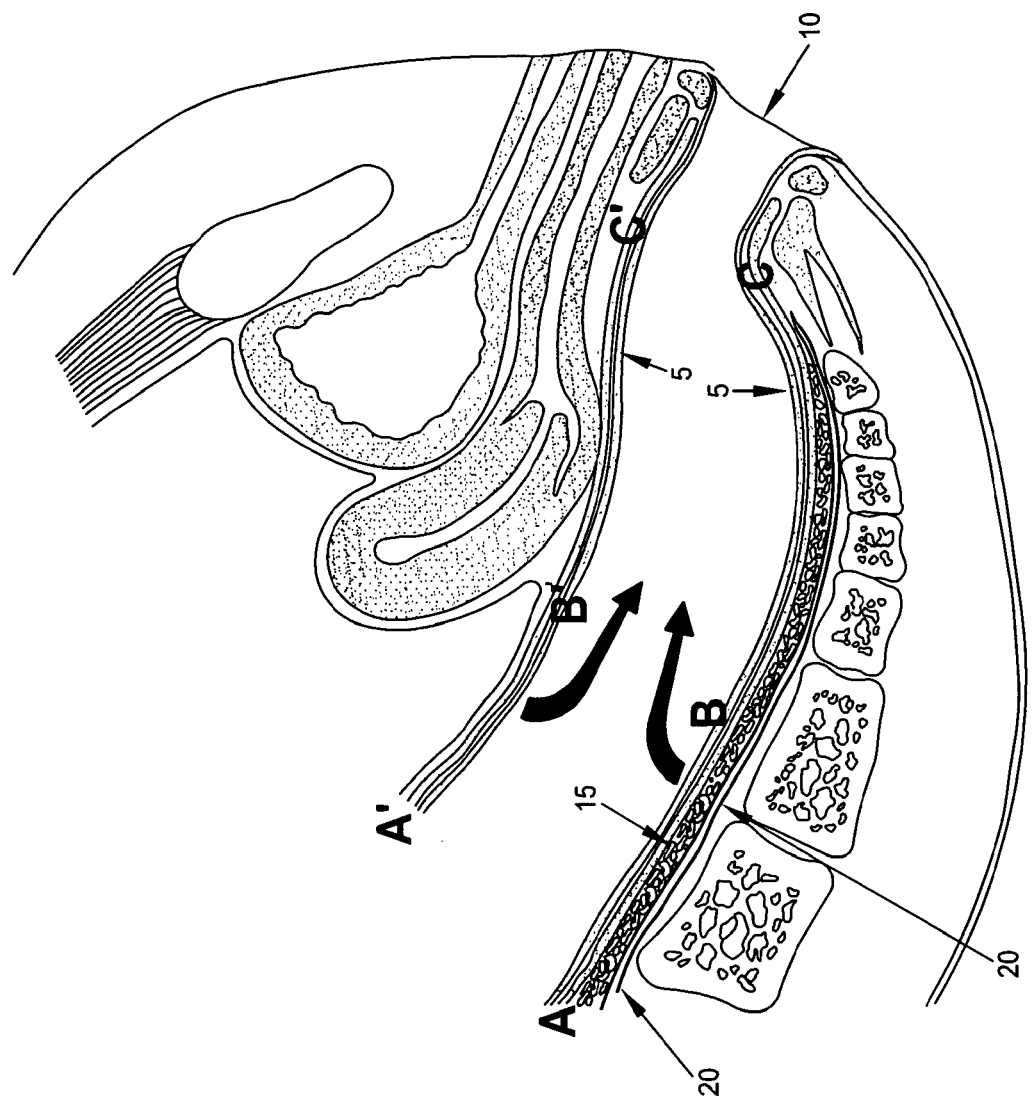
FIG. 2 is a schematic view of normal rectal anatomy, as seen in mid-sagittal view.
Figure 7:
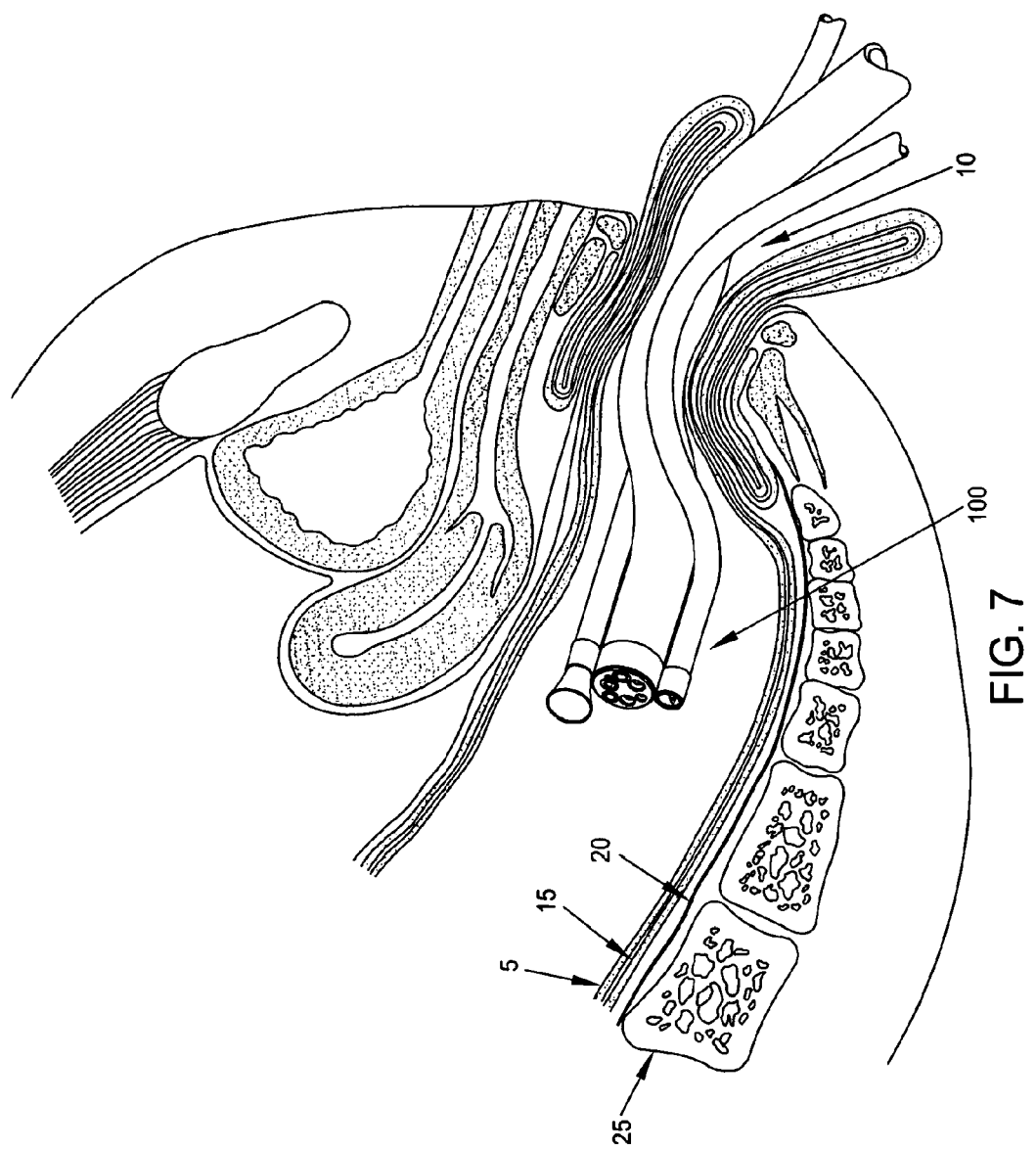
FIG. 7 is a schematic view showing the novel endoscope assembly of FIG. 5 deployed in the rectum.

Looking first at FIGS. 1 and 2, there is shown a schematic view of normal rectal anatomy. More particularly, it will be seen that the rectum 5 generally comprises an elongated tubular structure terminating in the anus 10. Along its length, rectum 5 is lined by the mesorectum 15, i.e., the mesentery of the rectum. Along part of its length, mesorectum 15 lies adjacent to the presacral fascia 20 which lines the sacrum 25 (FIG. 7).

Figure 3:
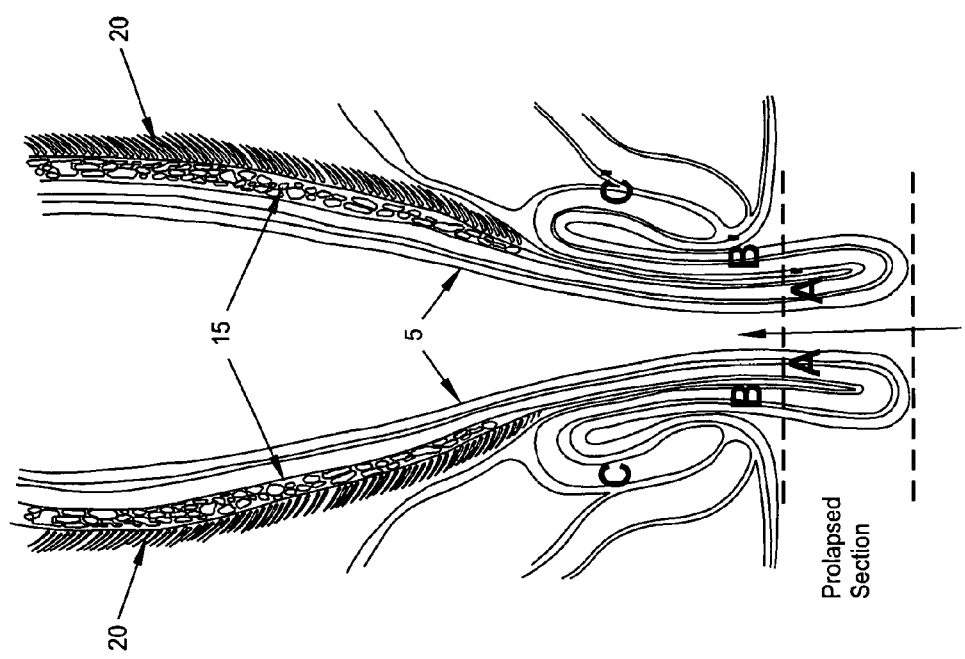
FIG. 3 is a schematic view of prolapsed rectal anatomy, as seen in coronal view.
Figure 4:
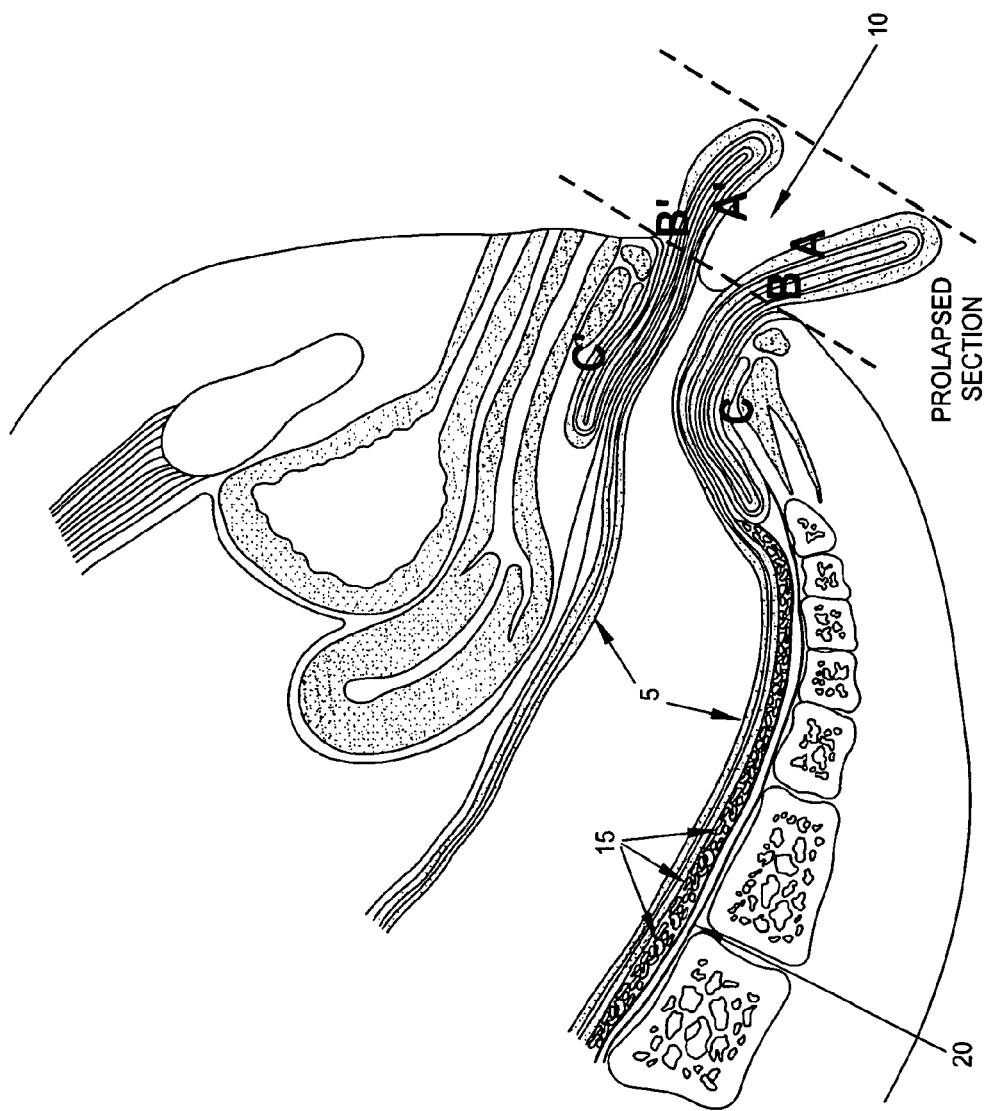
FIG. 4 is a schematic view of prolapsed rectal anatomy, as seen in mid-sagittal view.

In the case of a prolapsed rectum, and looking now at FIGS. 3 and 4, the walls of rectum 5 are not properly held in place, so that the rectum prolapses towards anus 10. In this respect it should be appreciated that FIGS. 3 and 4 show a so-called "full thickness rectal prolapse" (i.e., where the entire rectum protrudes through the anus), however, these views are intended to be merely exemplary and it should be appreciated that the present invention is applicable to other forms of rectal prolapse as well, i.e., "mucosal prolapse" where only the rectal mucosa prolapses and/or "internal intussusception" where the rectum may collapse but not protrude through the anus.

The present invention provides a new and improved approach for treating rectal prolapse, wherein the surgery is performed endoscopically so as to minimize trauma for the patient.

Figure 5:
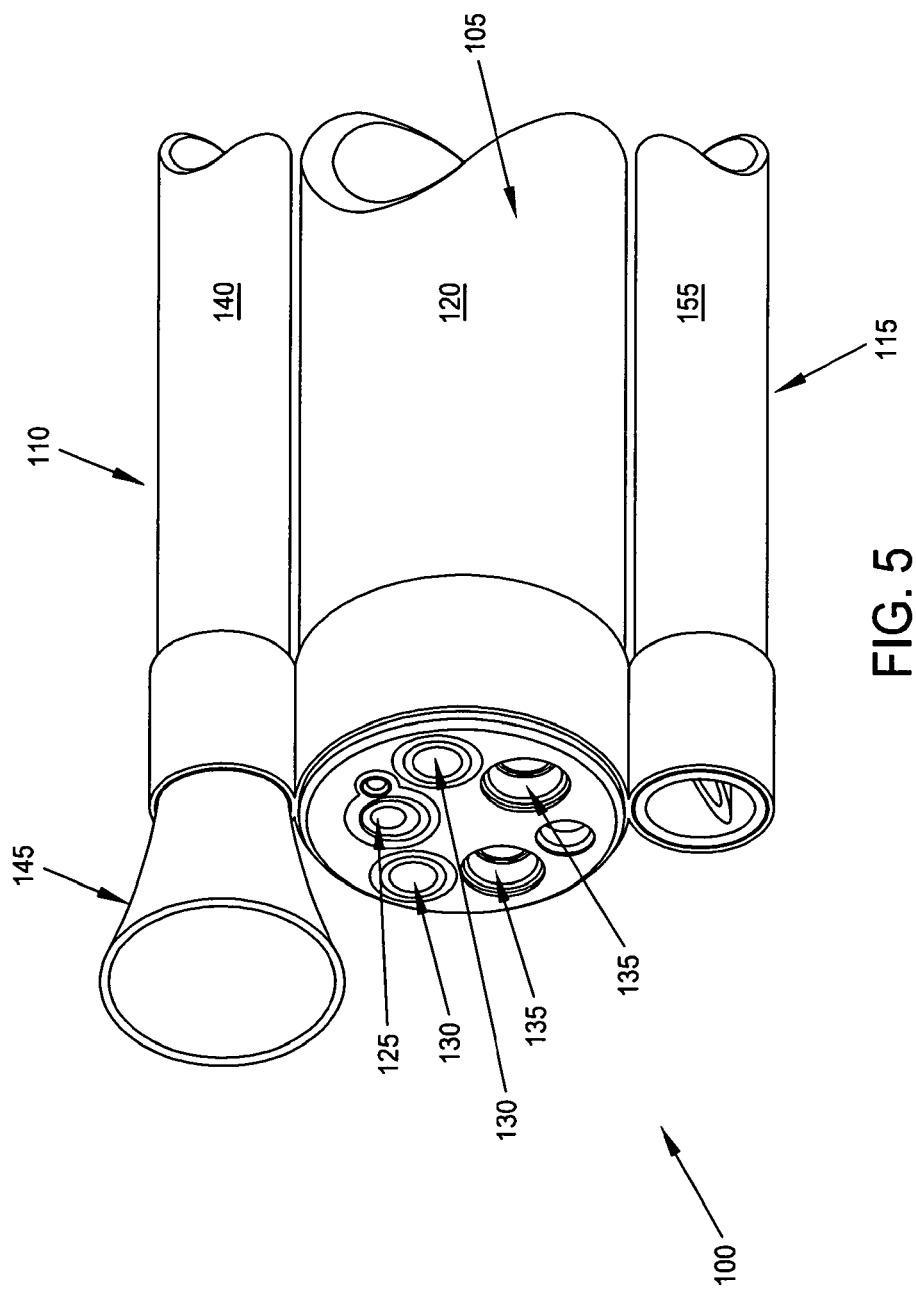
FIG. 5 is a schematic view of a novel endoscope assembly, wherein the novel endoscope assembly comprises an endoscope, a balloon catheter and a fastener deployment device.

More particularly, and looking now at FIG. 5, there is shown a novel endoscope assembly 100 formed in accordance with the present invention. Endoscope assembly 100 generally comprises an endoscope 105 for visualizing the interior of the rectum, a balloon catheter 110 for selectively deploying a balloon within the interior of the rectum, and a fastener deployment device 115 for selectively fastening the rectum to supporting structure, all as will hereinafter be discussed in further detail. Endoscope assembly 100 is preferably constructed so that endoscope 105, balloon catheter 110 and fastener deployment device 115 are mounted together for insertion into the rectum as a unit.

Endoscope 105 may comprise a conventional endoscope. By way of example but not limitation, endoscope 105 may comprise a shaft 120 comprising a viewing element 125, lighting elements 130, working lumens 135, etc.

Balloon catheter 110 may comprise a conventional balloon catheter. By way of example but not limitation, balloon catheter 110 may comprise a shaft 140 terminating in a distal end 145 from which a balloon (not shown in FIG. 5) may be selectively deployed, as will hereinafter be discussed in further detail.

Fastener deployment device 115 may comprise a tacker or fastener for tacking or fastening tissue. By way of example but not limitation, fastener deployment device 115 may comprise a shaft 155 containing a fastener (not shown in detail in FIG. 5) for fastening tissue, as will hereinafter be discussed in further detail.

Figure 6:
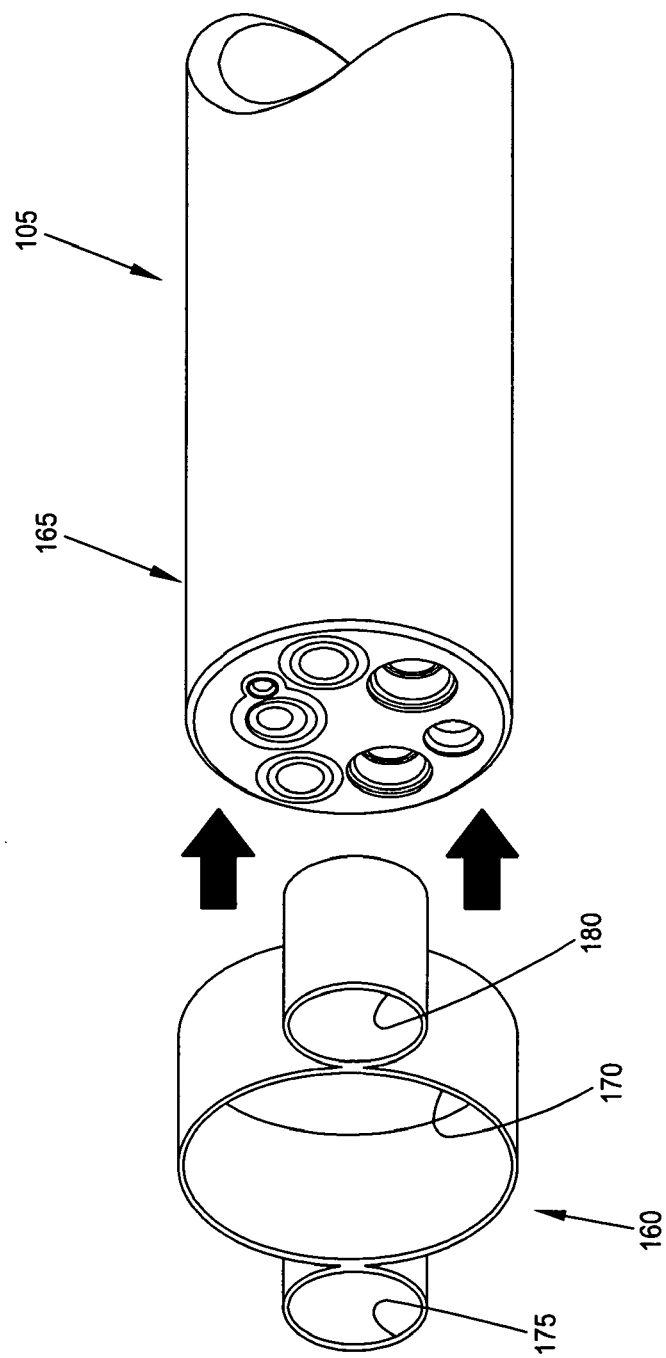
FIG. 6 is a schematic view showing how a distal mount may be secured to the distal end of a conventional endoscope in order to permit the balloon catheter and fastener deployment device to be mounted to the endoscope.

In one preferred form of the invention, and looking now at FIGS. 5 and 6, endoscope assembly 100 may be formed by securing a distal mount 160 to the distal end 165 of endoscope 105. To this end, distal mount 160 may comprise a central opening 170 sized to fit over distal end 165 of endoscope 105. Distal mount 160 preferably also comprises a first lateral opening 175 for slidably receiving shaft 140 of balloon catheter 110 therein, and a second lateral opening 180 for slidably receiving shaft 155 of fastener deployment device 115 therein.

Endoscope assembly 100 is preferably used in the following manner to endoscopically treat rectal prolapse.

First, and looking now at FIG. 7, endoscope assembly 100 is advanced into rectum 5 via anus 10.

Figure 8:
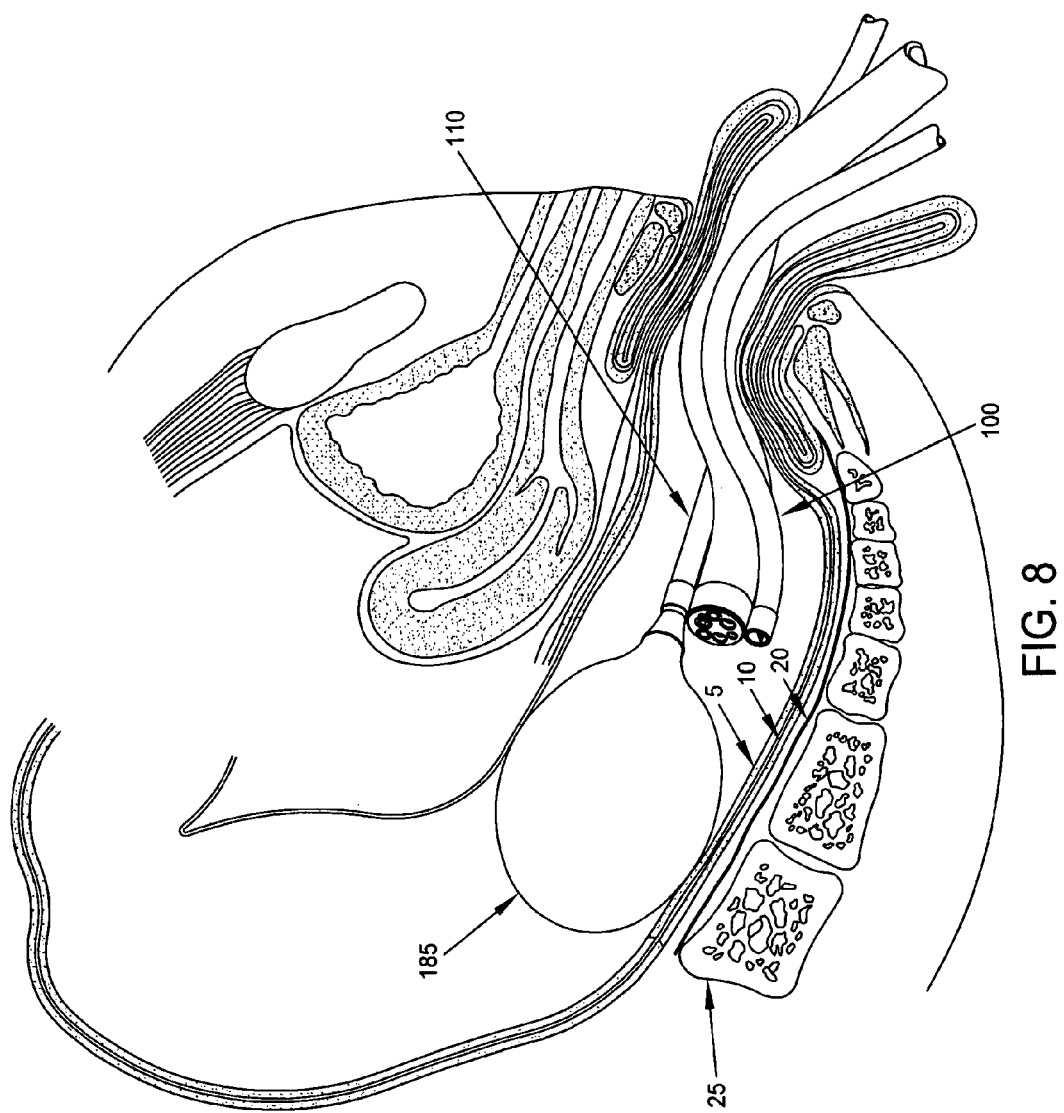
FIG. 8 is a schematic view like that of FIG. 7, except showing the balloon of the balloon catheter having been inflated.

Next, and looking now at FIG. 8, balloon 185 of balloon catheter 110 is inflated so as to securely engage, and thereby "grip", rectum 5.

Figure 9:
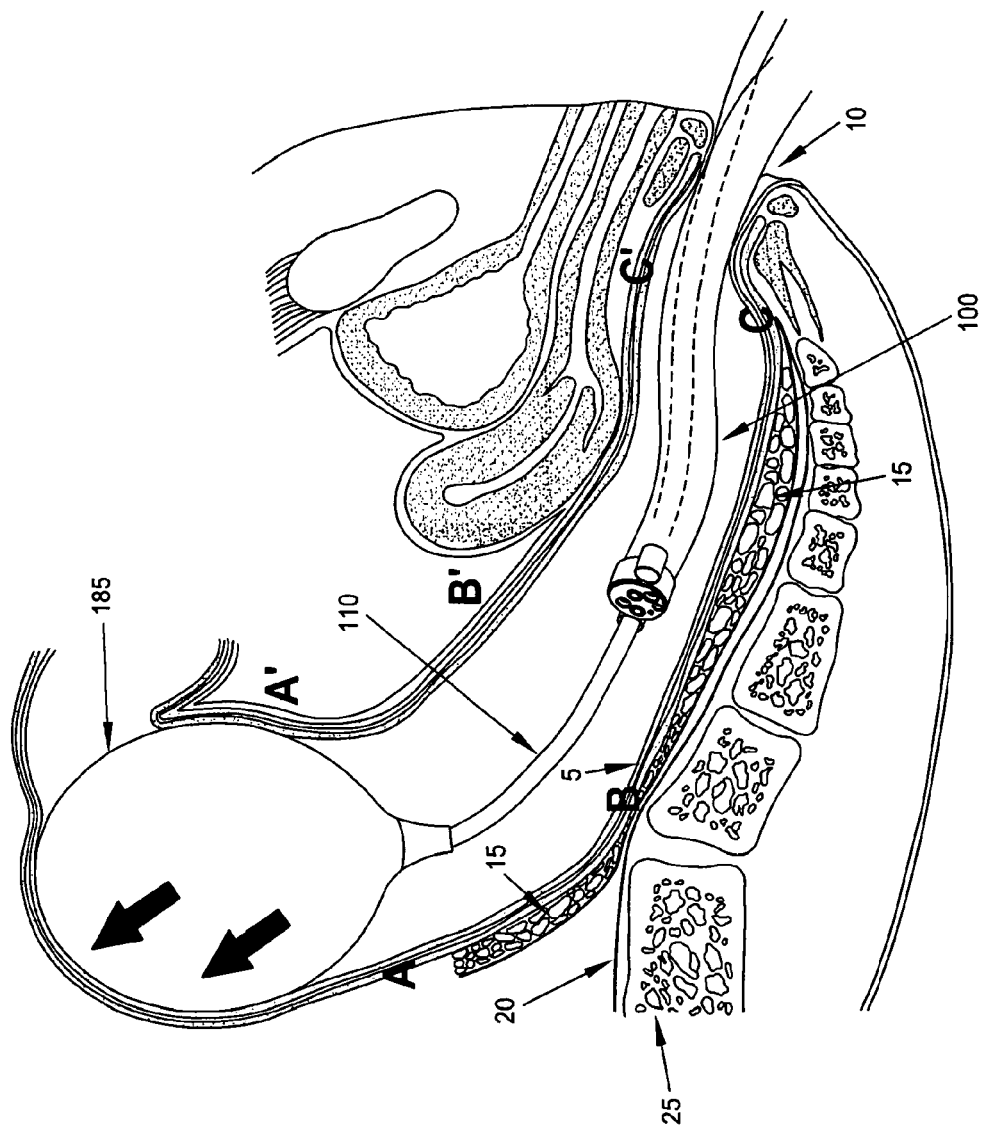
FIG. 9 is a schematic view like that of FIG. 8, except showing the balloon of the balloon catheter having been extended distally from the endoscope so as to reduce rectal prolapse.

Then, and looking now at FIG. 9, balloon catheter 110 is advanced distally relative to the remainder of endoscope assembly 100, e.g., by pushing on the proximal end of shaft 140 of balloon catheter 110, whereby to cause shaft 140 of balloon catheter 110 to slide distally within first lateral opening 175 of distal mount 160 and to cause balloon 185 to move distally within the body. As this occurs, the advancing balloon 185 of balloon catheter 110 carries with it rectum 5, since balloon 185 securely engages and grips rectum 5, thereby reducing the prolapse. Preferably, balloon catheter 110 is moved distally by a sufficient distance so as to return the prolapsed rectum to its normal, non-prolapsed state.

Figure 10:
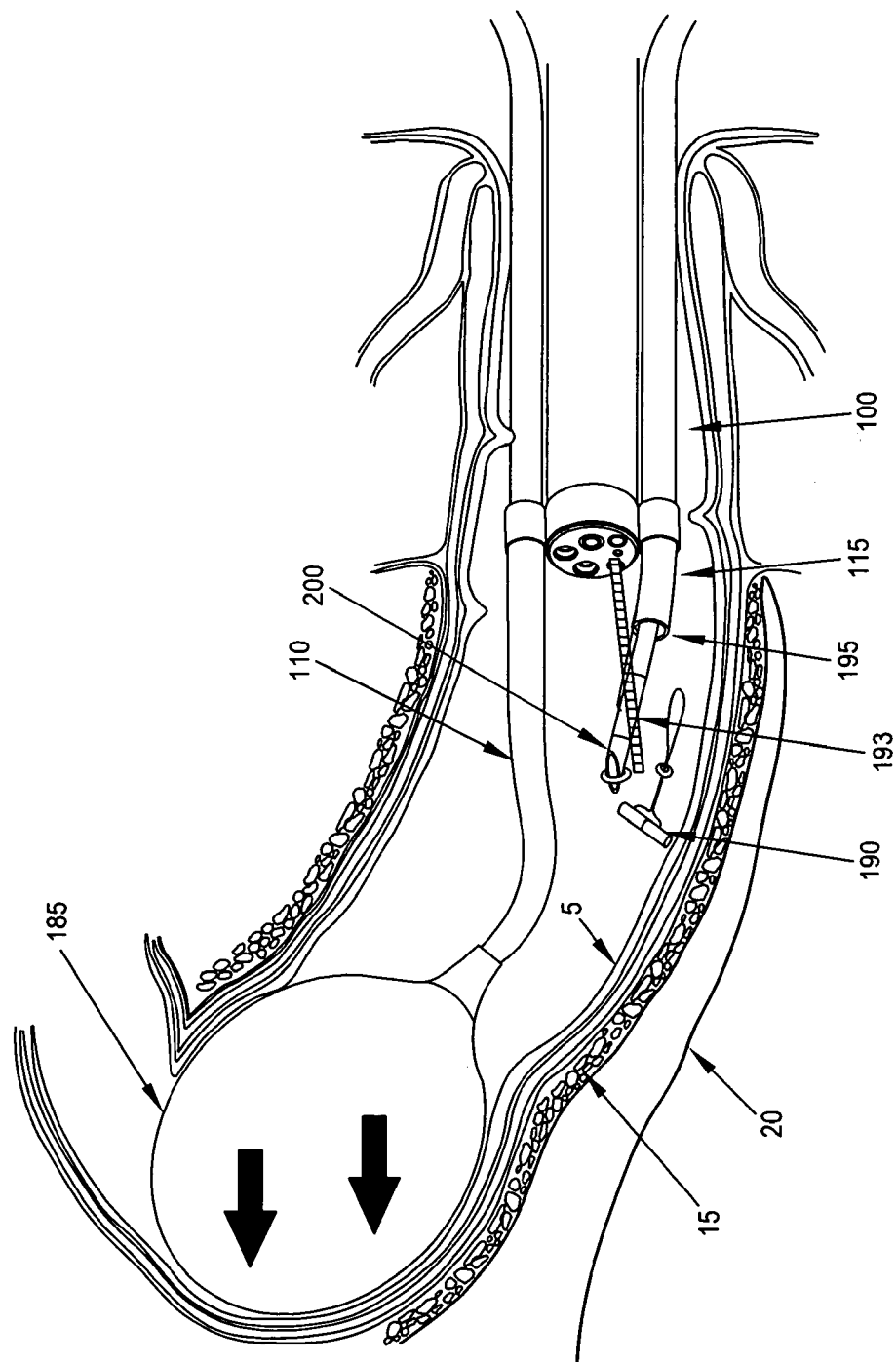

Then, and looking now at FIG. 10, fastener deployment device 115 is used to secure rectum 5 to supporting tissue, whereby to retain rectum 5 in its normal, non-prolapsed state.

In one preferred form of the invention, and looking now at FIGS. 10-12, fastener deployment device 115 is used to fasten rectum 5 and mesorectum 15 to presacral fascia 20 using one or more tacks 190. In this respect it will be appreciated that it is generally desirable to secure rectum 5 and mesorectum 15 to presacral fascia 20, since the presacral fascia generally constitutes excellent supporting tissue. Of course, if desired, rectum 5 and mesorectum 15 may also be secured to other supporting tissue as well (e.g. anterior abdominal wall). To this end, an ultrasound probe 193 (shown in FIG. 10, but omitted from FIGS. 11 and 12 for viewing clarity) may be advanced through a working lumen 135 of endoscope 105 so as to locate the sacral promontory (or other satisfactory anatomical landmark), and then shaft 155 of fastener deployment device 115 may be advanced relative to the remainder of endoscope assembly 100 (e.g., by sliding shaft 155 of fastener deployment device 115 within second lateral opening 180 of distal mount 160) until the distal end 195 of fastener deployment device shaft 155 is proximate the tacking site. Then, a needle 200 is advanced out of fastener deployment device shaft 155 and passed through rectum 5, mesorectum 15 and presacral fascia 20. Next, a tack or fastening device 190 is ejected out of needle 200, and then needle 200 withdrawn back through presacral fascia 20, mesorectum 15 and rectum 5, leaving a length of filament 205 extending from tack 190 through the intervening tissue (i.e., through presacral fascia 20, mesorectum 15 and rectum 5) and into the interior of rectum 5. Filament 205 can then be tied off, or otherwise secured with a securement band 210, so as to secure rectum 5 and mesorectum 15 to presacral fascia 20. This process can then be repeated as necessary so as to set additional tacks or fasteners into the tissue, whereby to secure the prolapsed rectum in its normal, non-prolapsed state.

Figure 13:
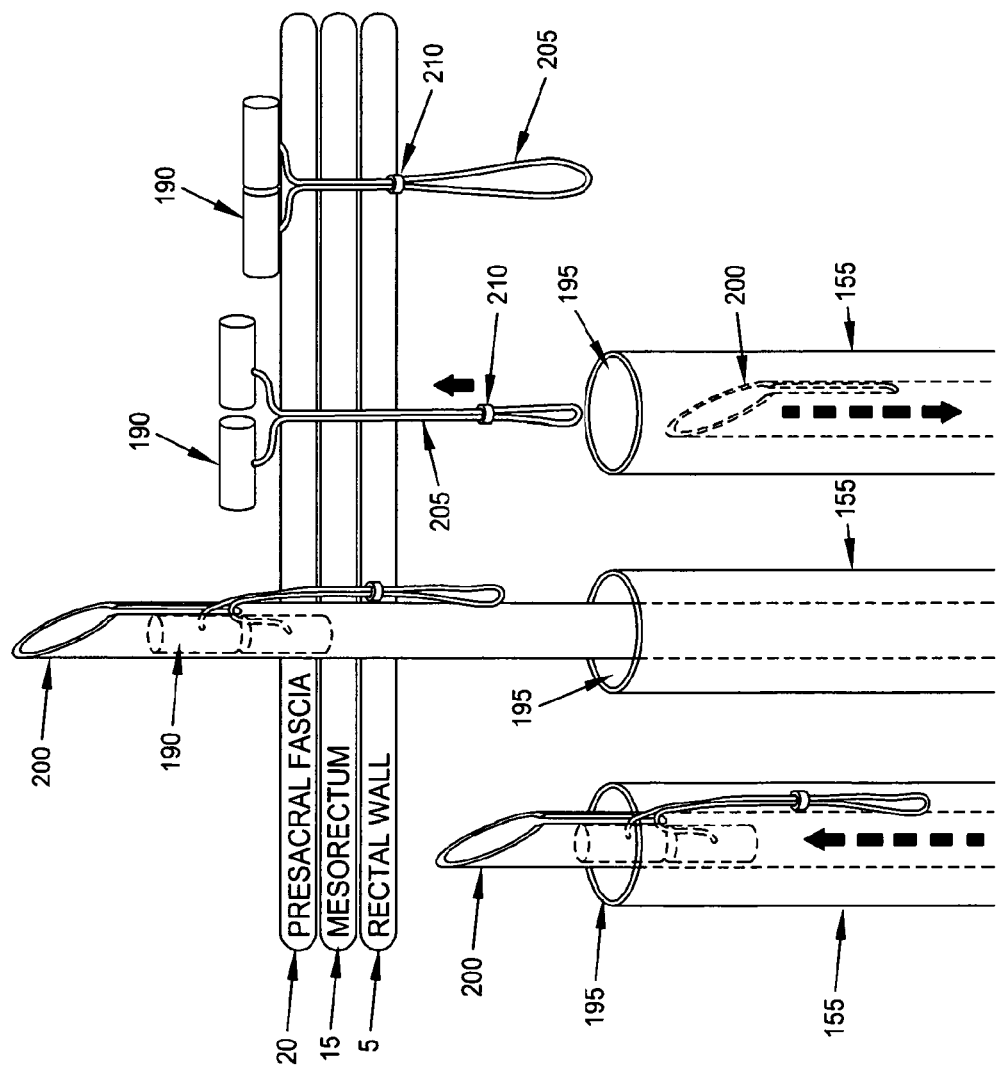
FIG. 13 is a schematic view showing operation of the fastener deployment device shown in FIGS. 10-12.

Further details of the operation of fastener deployment device 115 are shown in FIG. 13.

Thereafter, fastener deployment device 115 is retracted so that its needle 200 sits within fastener deployment device shaft 155, and then fastener deployment device shaft 155 is retracted so that its distal end 195 once again sits substantially adjacent to the distal end of endoscope 105. Then balloon 185 is deflated, and then balloon catheter 110 is retracted so that its distal end once again sits substantially adjacent to the distal end of endoscope 105. Then endoscope assembly 100 is withdrawn from the rectum via anus 10.

Figure 14:
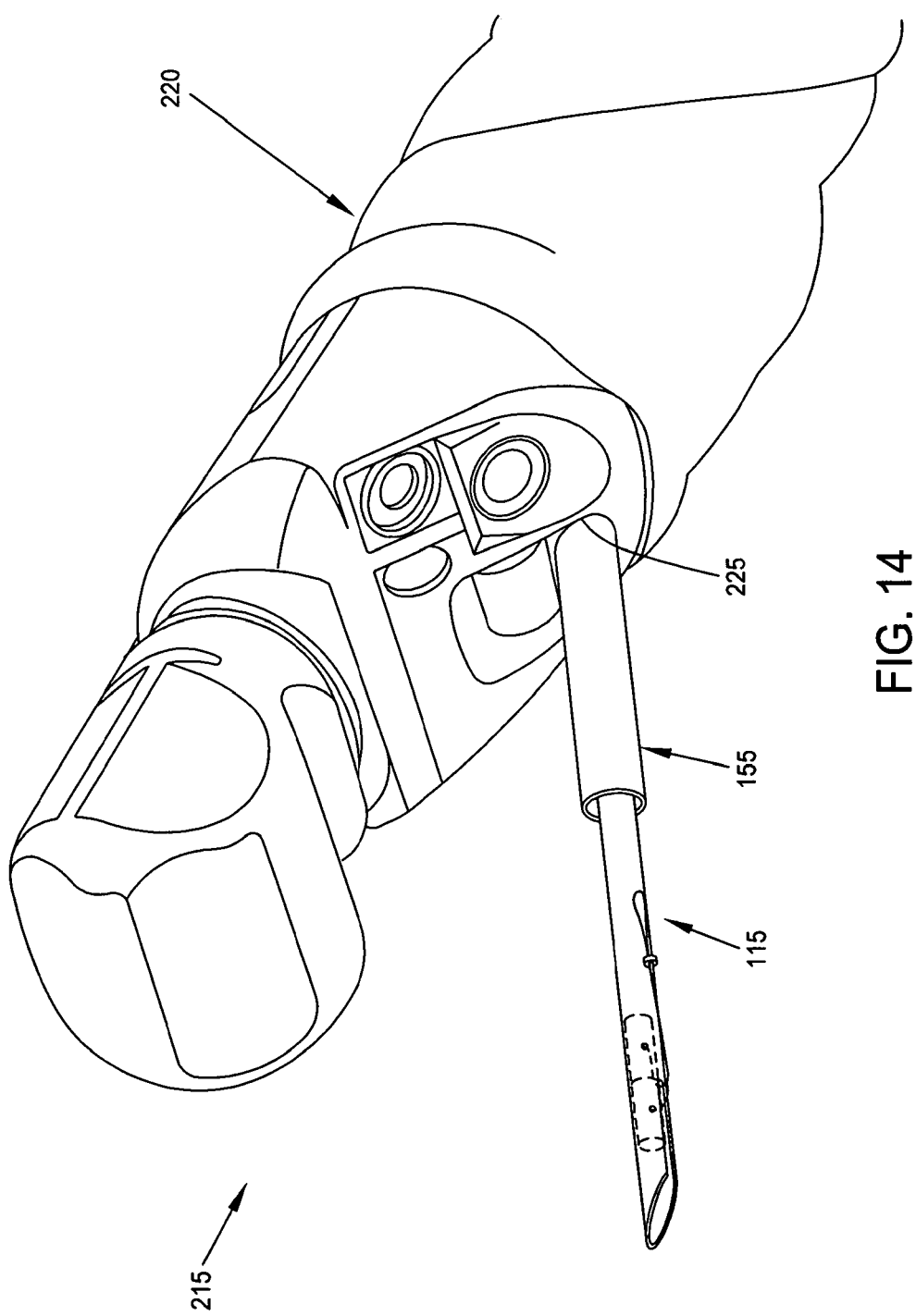
FIG. 14 is a schematic view showing a combined ultrasound probe/fastener deployment device.

Looking next at FIG. 14, there is shown a combined ultrasound probe/fastener deployment device 215. More particularly, combined ultrasound probe/fastener deployment device 215 generally comprises an ultrasound probe 220 having a working lumen 225 formed therein. Fastener deployment device 115 has its shaft 155 slidably disposed within working lumen 225 so that the fastener deployment device can be selectively advanced out of ultrasound probe 220. In this form of the invention, combined ultrasound probe/fastener deployment device 215 can be movably mounted to endoscope assembly 100 (e.g., by an appropriately configured distal mount 160), or combined ultrasound probe/fastener deployment device 215 can be advanced through a working lumen 135 of endoscope 105, or combined ultrasound probe/fastener deployment device 215 can be advanced into rectum 5 independently of endoscope 105.

It should also be appreciated that, if desired, balloon catheter 110 can be advanced through a working lumen 135 of endoscope 105, or balloon catheter 110 can be advanced into rectum 5 independently of endoscope 105.

Furthermore, it should also be appreciated that, if desired, fastener deployment device 115 can be advanced through a working lumen 135 of endoscope 105, or fastener deployment device 115 can be advanced into rectum 5 independently of endoscope 105.

Figure 15:
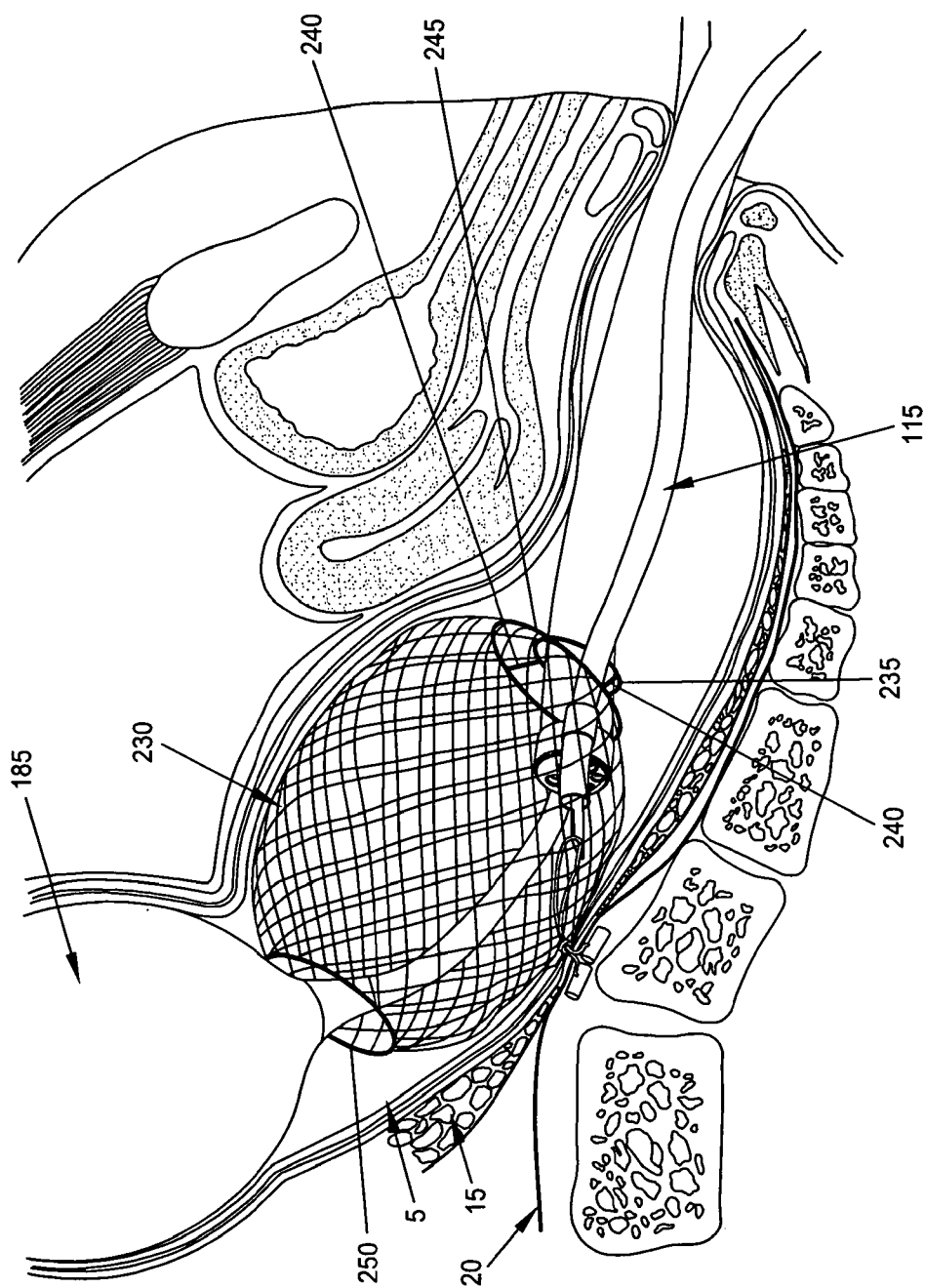
FIG. 15 is a schematic view showing an alternative approach for treating a prolapsed rectum.

Looking next at FIG. 15, in an alternative form of the invention, an expandable net 230 may be deployed within rectum 5 (e.g., after balloon 185 has been used to return the prolapsed rectum to its normal, non-prolapsed state but before fastener deployment device 115 has been used to secure rectum 5 to supporting tissue) in order to better hold rectum 5 in position while fastening occurs. In this respect it should also be appreciated that expandable net 230 can also serve to help anchor the endoscope and hold it in place while fastening is effected, thereby facilitating the fastening process. In one preferred form of the invention, expandable net 230 may comprise a collar 235 configured to ride over shaft 120 of endoscope 105, with struts 240 connecting collar 235 to a proximal support ring 245. Preferably, a distal support ring 250 is formed on the distal end of expandable net 230. It should be appreciated that various approaches can be used to hold expandable net 230 in a contracted position prior to expansion. By way of example but not limitation, expandable net 230 may be formed out of Nitinol, and a temperature transition used to transform expandable net 230 from its contracted position to its expanded position.

If desired, balloon catheter 110 can be replaced by an alternative rectum-gripping mechanism, e.g., wherein expandable arms, an expandable frame, etc. are erected within the rectum so as to grip the rectum prior to the distal movement necessary to return the prolapsed rectum to its normal, non-prolapsed state. In this respect it will be appreciated that while it is generally preferred to use a balloon for engaging and pushing the rectum, such alternative rectum-gripping mechanisms (e.g., expandable arms, an expandable frame, etc.) may offer the advantage of better engaging the tissue of the rectum and may provide mechanical advantage for pushing the rectum distally. In this respect it should also be appreciated that while it is generally preferred that the balloon and/or alternative rectum-gripping mechanisms be relatively atraumatic, it may also be desirable to provide tissue-gripping means to facilitate pushing the prolapsed rectum distally. To this end, where a balloon is used, it may be desirable to provide the balloon with a high-friction outer surface; and where expandable arms are used, it may be desirable to provide the arms with tissue-gripping elements (e.g., mechanical jaws, suction mechanisms, etc.); and where an expandable frame is used, it may be desirable to provide openings in the frame to facilitate tissue engagement, etc.

Furthermore, if desired, fastener deployment device 115 can be replaced by other fastener deployment devices. In this respect it should be appreciated that the terms "fastener", "fastener deployment device", "tack" and "tacker" are intended to encompass substantially any mechanical structure which is capable of securing the rectum to supporting tissue. By way of example but not limitation, the terms "fastener", "fastener deployment device", "tack" and "tacker" are intended to encompass shaft-type tacks, legged staples, multi-part fasteners, tacks comprising a body having suture extending therefrom, etc.

Furthermore, if desired, fastener deployment device 115 can be replaced by appropriate endoscopic suturing apparatus, with the rectum being secured to supporting tissue using conventional suture.

Figure 16:
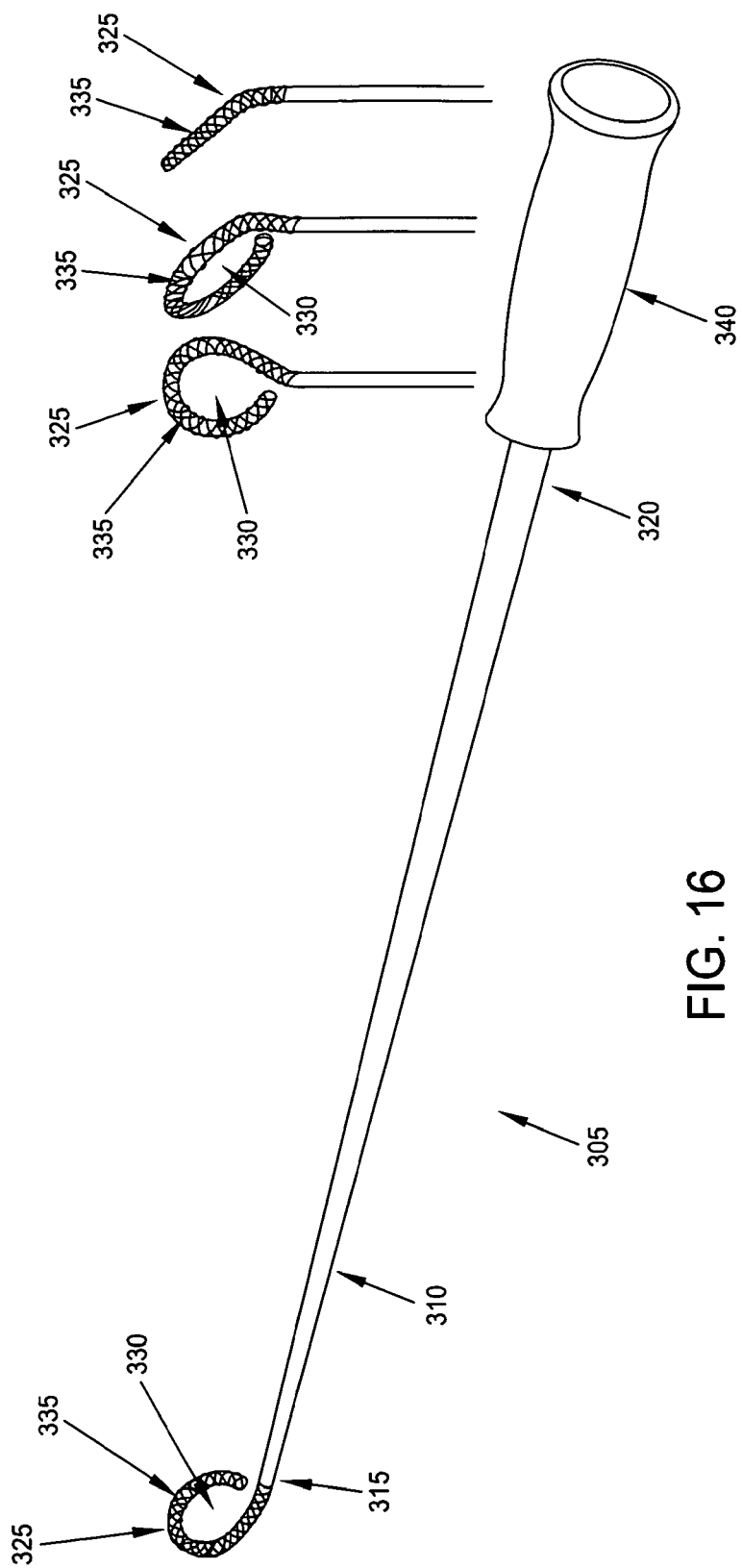
FIG. 16 is a schematic view of a novel prolapse treatment instrument formed in accordance with the present invention.

In another embodiment, and looking next at FIG. 16, there is shown a novel prolapse treatment instrument 305 which may be used to treat rectal prolapse.

Prolapse treatment instrument 305 generally comprises a shaft 310 having a distal end 315 and a proximal end 320. Attached to distal end 315 of shaft 310 is a tissue support 325 for engaging the interior wall of the rectum and repositioning the same, as will hereinafter be discussed. Tissue support 325 is preferably configured so as to define an opening 330 therethrough. Opening 330 permits a tissue fixation device (e.g., such as the fastener deployment device 115 described previously) to directly access the portion of the rectum engaged by tissue support 325, as will also hereinafter be discussed. In one preferred form of the present invention, tissue support 325 is configured in the form of a generally circular shape, with opening 330 being located in the middle of tissue support 325. Preferably, the exterior of tissue support 325 includes a texturing 335 which enhances the ability of tissue support 325 to atraumatically engage the interior wall of the rectum and permit manipulation thereof. In one preferred form of the invention, texturing 335 comprises a suture or other filament secured to the exterior surface of tissue support 325, whereby to provide a surface profile to the exterior surface of tissue support 325. Alternatively, texturing 335 may comprise a layer of foam, fabric, or other material, etc. secured to tissue support 325. A handle 340 is secured to proximal end 320 of shaft 310, whereby to permit a surgeon to manipulate the working end of prolapse treatment instrument 305, as will hereinafter be discussed.

Figure 17:
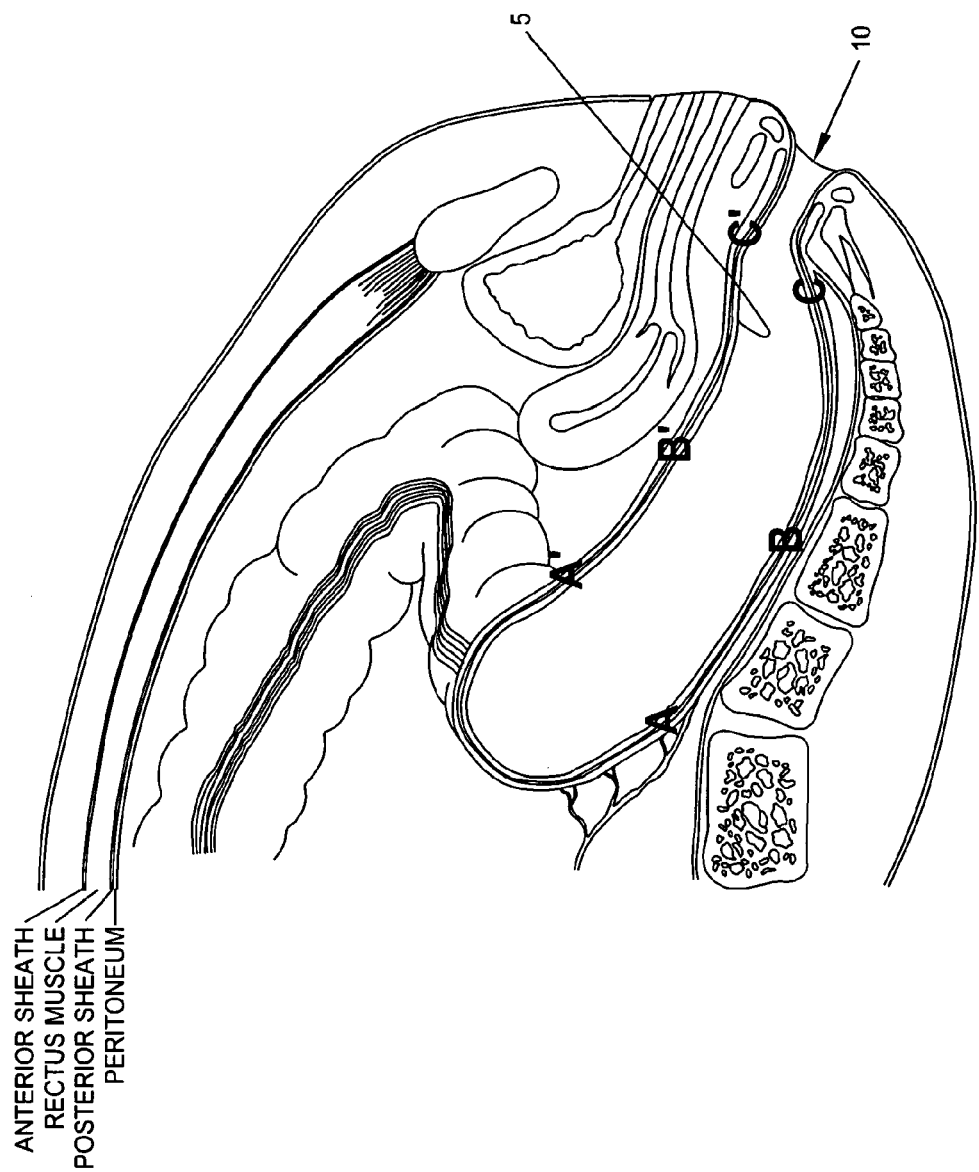
FIGS. 17 and 18 illustrate an exemplary case of rectal prolapse.
Figure 18:
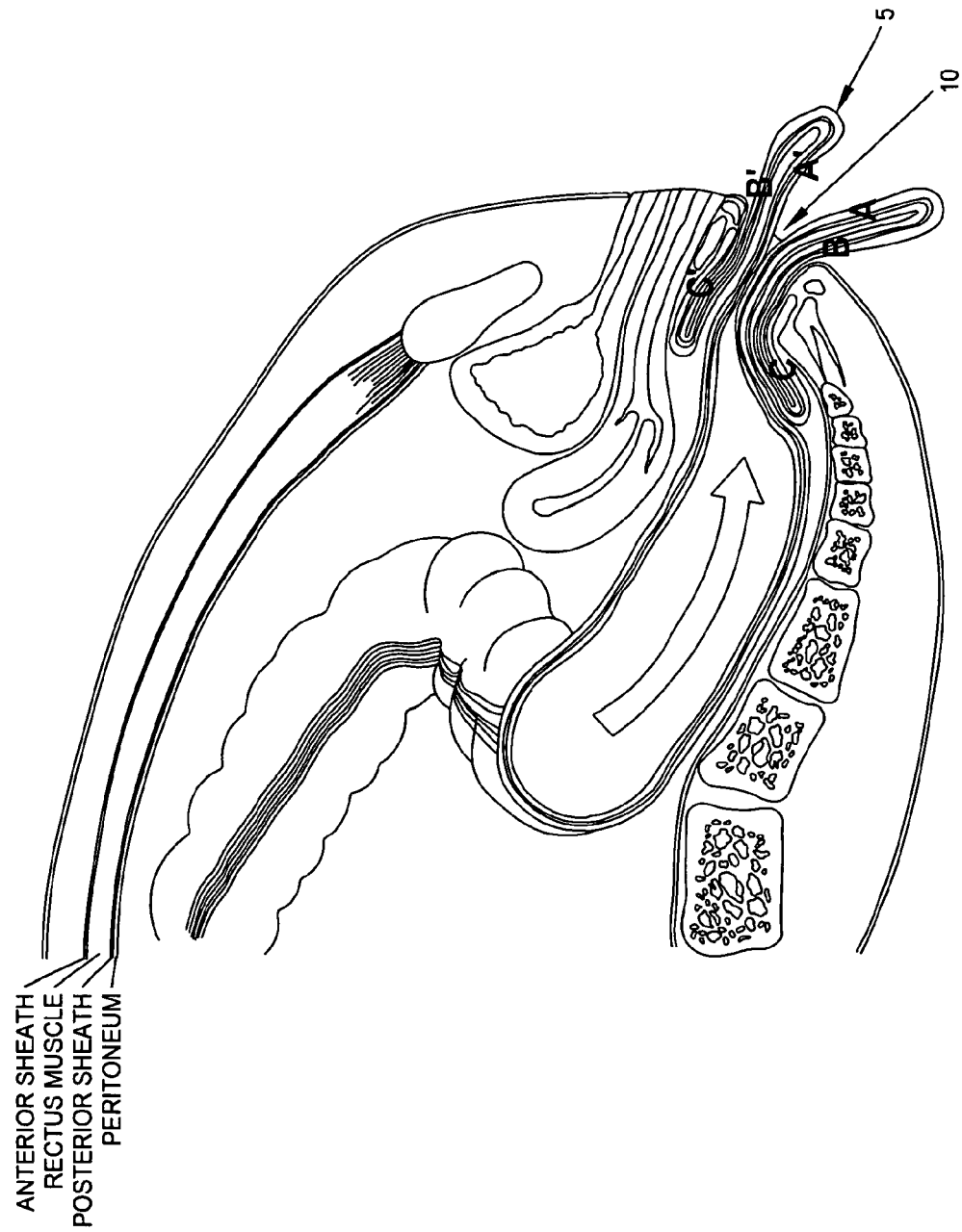

Looking next at FIGS. 17 and 18, there is shown an exemplary case of rectal prolapse, wherein rectum 5 prolapses towards (and in this case, completely out of) anus 10. Note how the reference points A-A', B-B' and C-C' on rectum 5 migrate toward (and in the case of reference points A-A' and B-B', completely through) the anus due to the rectal prolapse condition.

As seen in FIGS. 19-26, novel prolapse treatment instrument 305 may be used to treat rectal prolapse.

Figure 19:
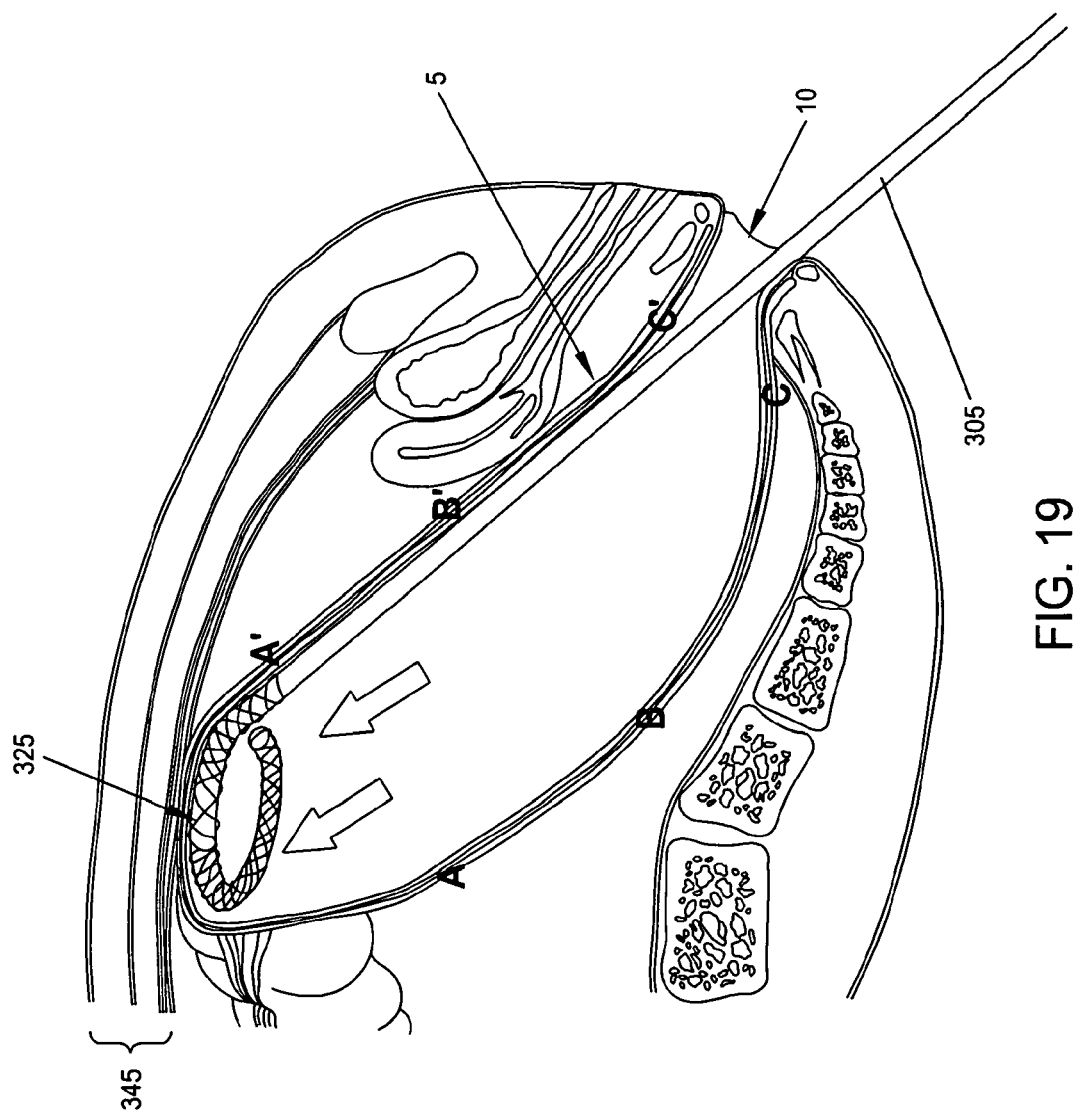
FIGS. 19-26 are schematic views showing the prolapse treatment instrument of FIG. 16 treating rectal prolapse.
Figure 20:
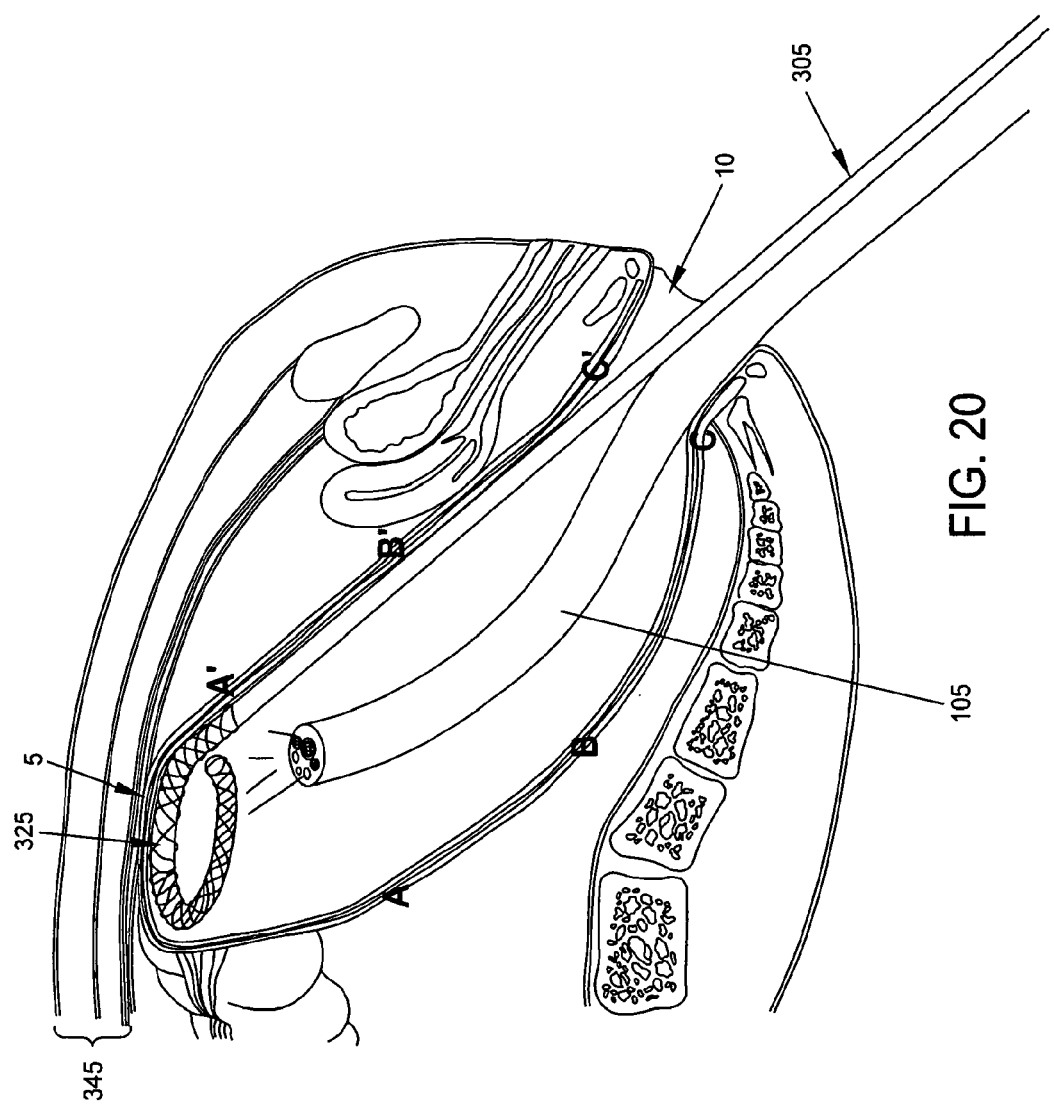
Figure 21:
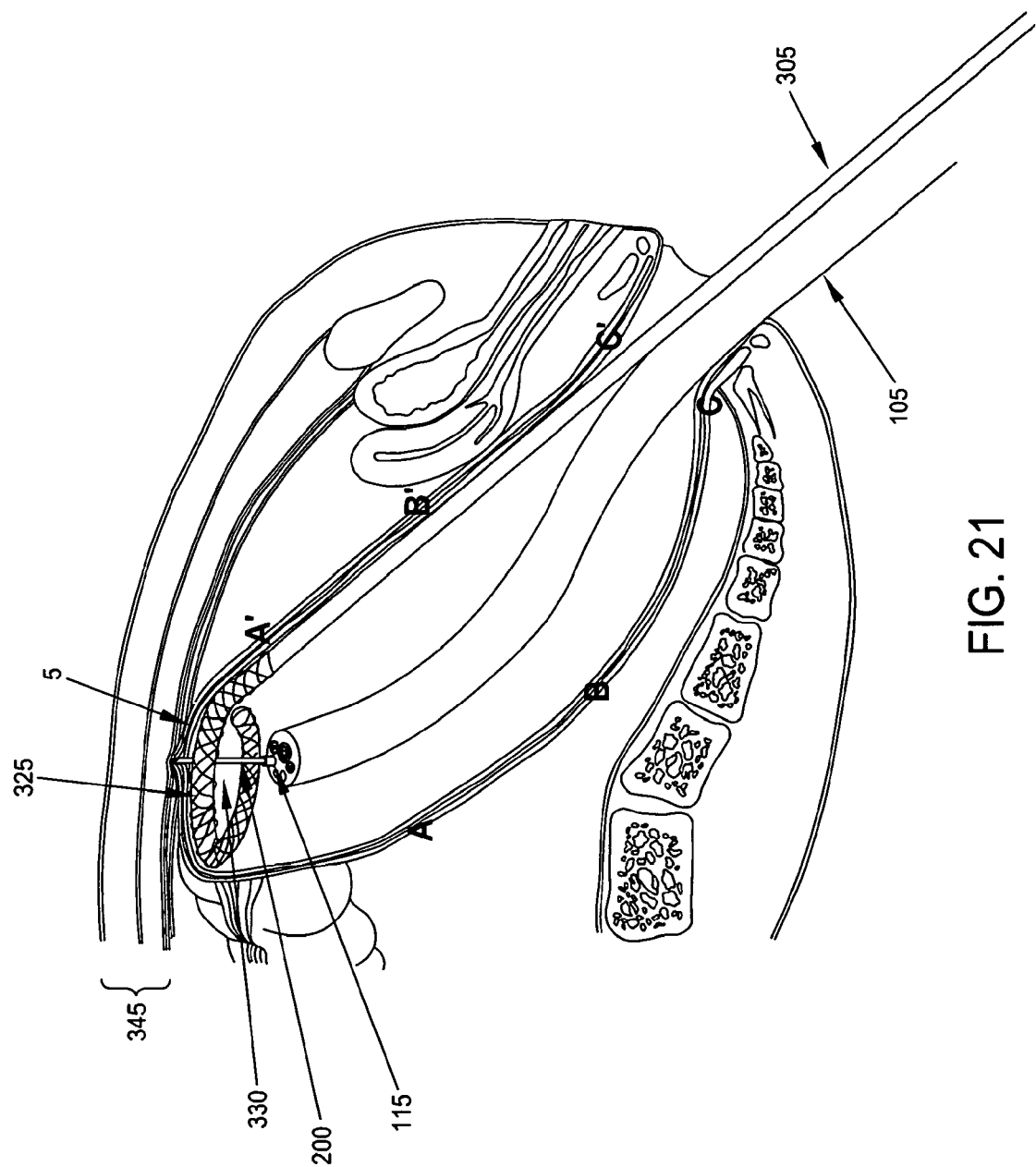

More particularly, as seen in FIG. 19, prolapse treatment instrument 305 is inserted into rectum 5 through anus 10. Using handle 340, the surgeon causes tissue support 325 to engage the interior wall of the prolapsed rectum and push it back up into place (note how this action causes the reference points A-A', B-B' and C-C' to return from their prolapsed positions in FIG. 18 to their natural positions in FIG. 17). To this end, texturing 335 allows tissue support 325 to atraumatically engage the interior wall of the rectum so that the wall of the rectum can be pressed up against stable tissue, e.g., the anterior abdominal wall 345. Preferably, as this is done, an endoscope 105 is also advanced into rectum 5 so as to provide visualization for the surgeon. See FIG. 20.

With prolapse treatment instrument 305 holding the repositioned rectum 5 in place, a tissue fixation device is used to secure the repositioned rectum 5 to anterior abdominal wall 345, preferably under the visualization provided by endoscope 105. In this respect it should be appreciated that opening 330 in tissue support 325 enables a tissue fixation device to directly access the portion of the rectum supported by prolapse treatment instrument 305 even while the rectum remains supported by prolapse treatment instrument 305. In other words, the construction of tissue support 325 is such that the rectum can be easily accessed for fixation purposes even as that tissue is supported by prolapse treatment instrument 305. Of course, it should also be appreciated that a tissue fixation device can access the supported tissue about the periphery of tissue support 325, rather than through the interior opening of tissue support 325, if desired.

In one preferred form of the invention, and looking now at FIGS. 21-26, the tissue fixation device comprises the fastener deployment device 115 described above.

Figure 22:
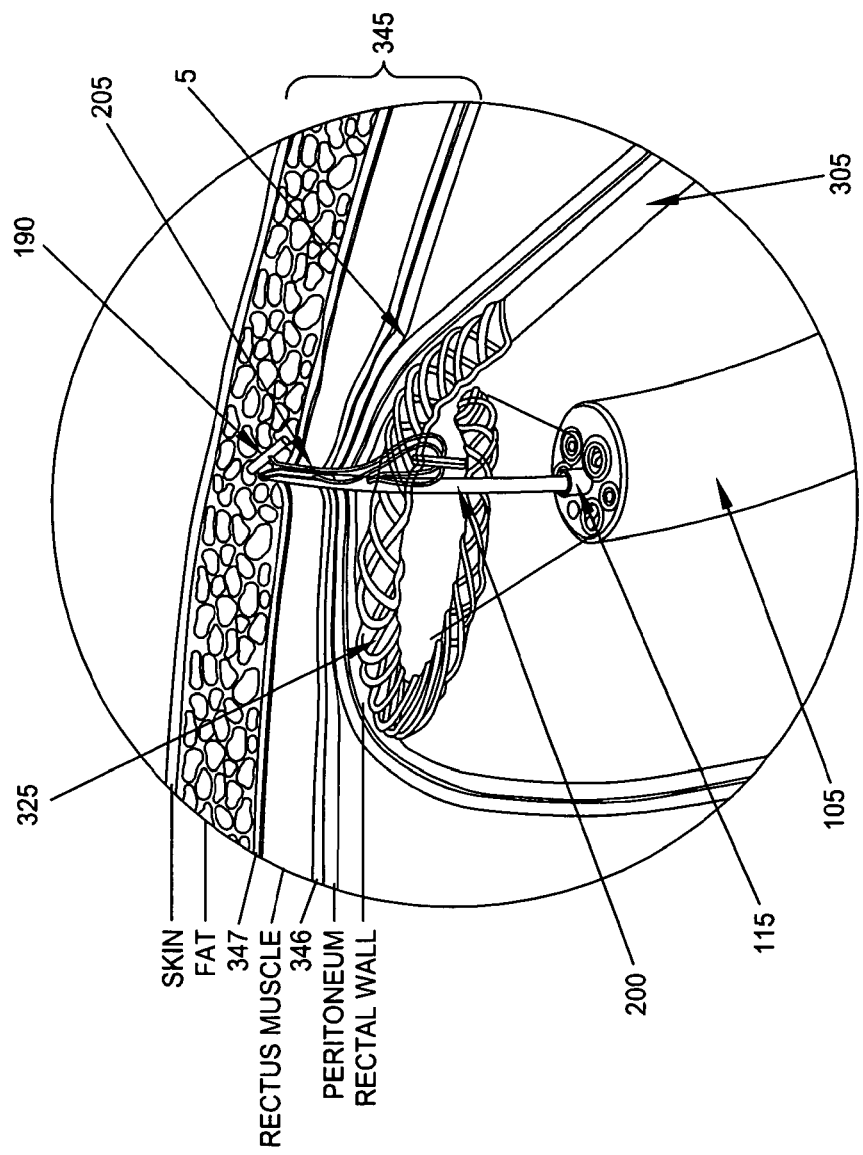
Figure 23:
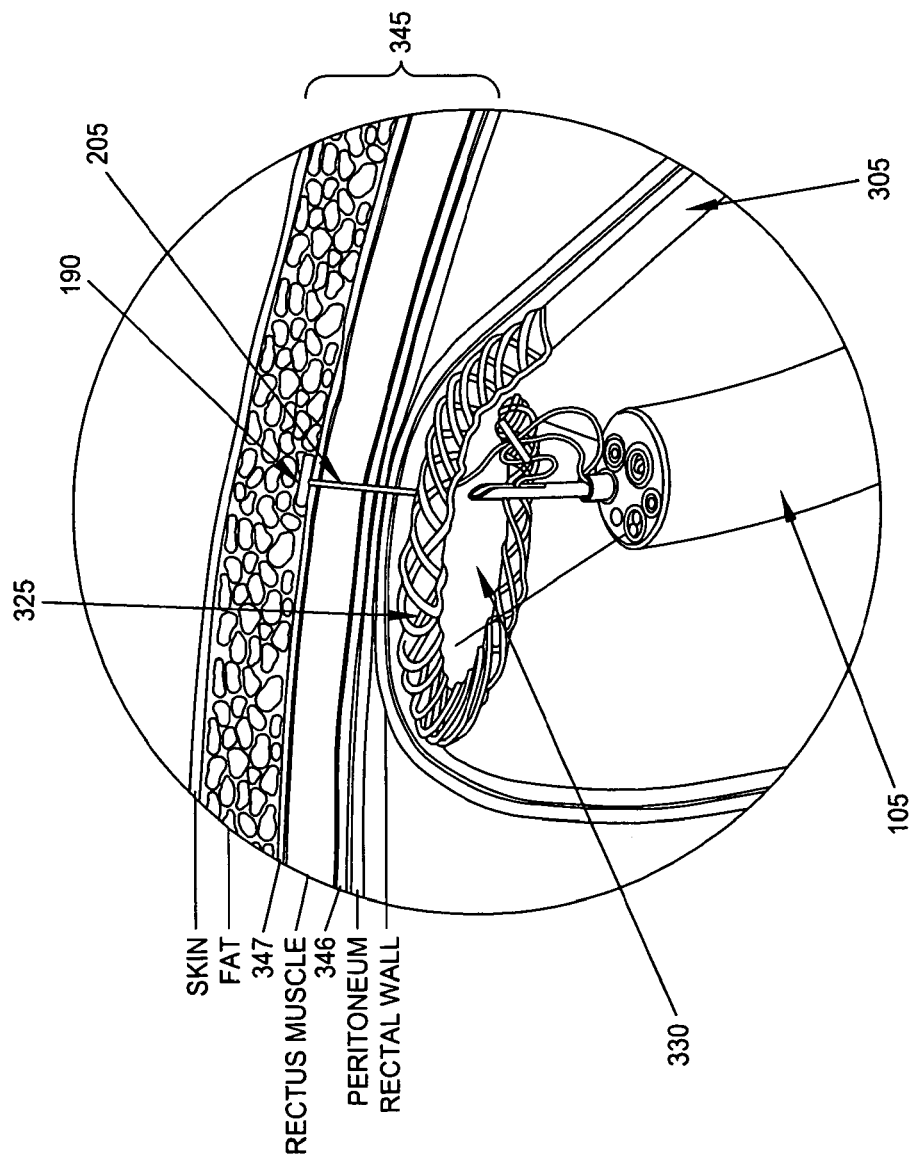
Figure 24:
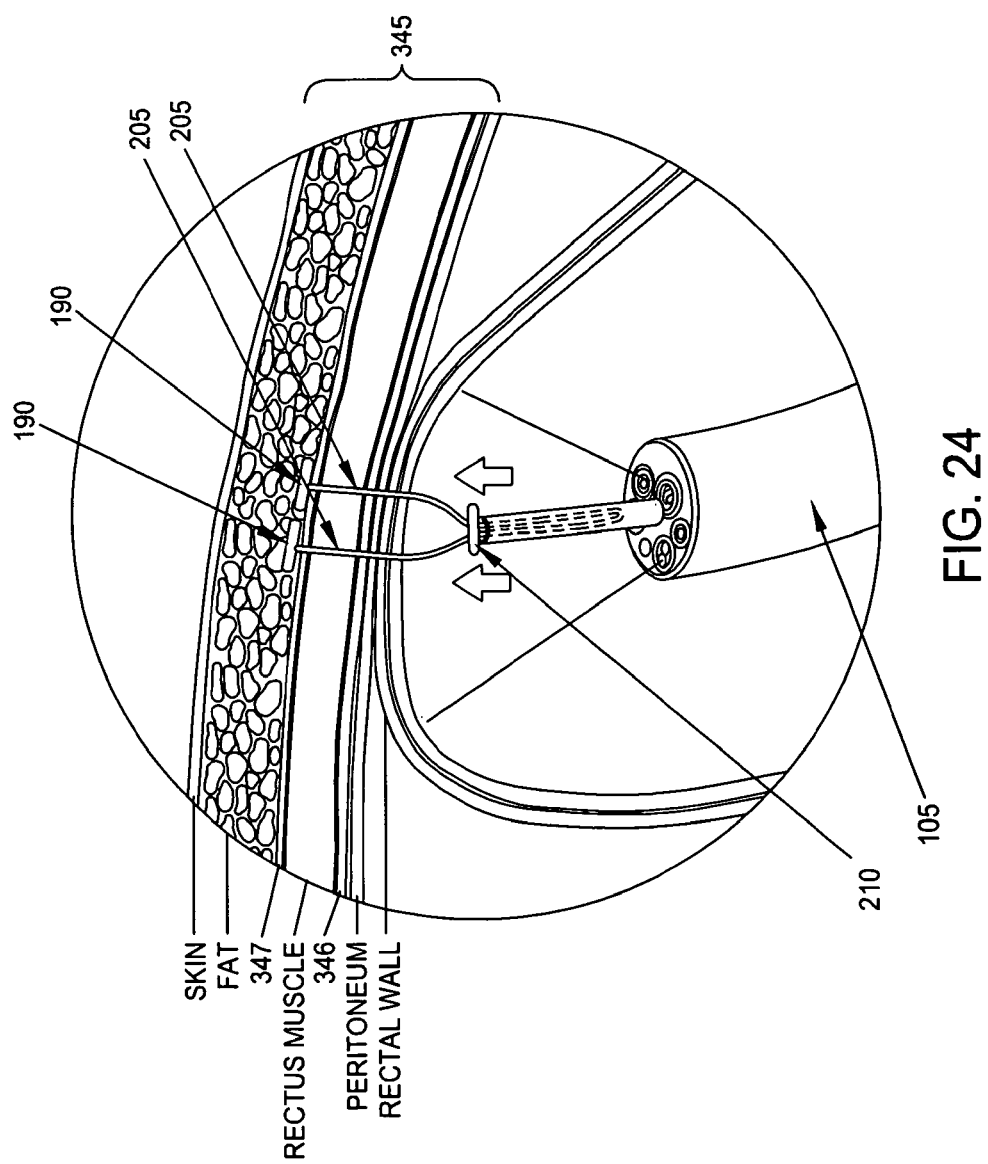

More particularly, in this form of the invention, a tacker needle 200 (FIG. 21) is advanced through opening 330 in tissue support 325, through rectum 5, and into anterior abdominal wall 345. Then a tack 190, having a length of filament 205 attached thereto, is ejected out of the distal end of needle 200 and into anterior abdominal wall 345 (FIG. 22). By way of example but not limitation, tack 190 may be ejected anterior to posterior sheath 346 or anterior to anterior sheath 347. Then needle 200 is withdrawn from anterior abdominal wall 345 and the side wall of rectum 5, and the length of filament 205 gently tensioned, so that the tack seats securely within anterior abdominal wall 345 (FIG. 23), with the length of filament 205 extending back into the interior of rectum 5. Needle 200 may then be repositioned, and thereafter advanced back through opening 330 in tissue support 325, through rectum 5 and into anterior abdominal wall 345, whereby to eject another tack 190 out of the distal end of needle 200, etc. At this point prolapse treatment instrument 305 may be removed from the surgical site (or, if preferred, kept in place), and a securement band 210 run up lengths of filament 205, so as to secure rectum 5 to anterior abdominal wall 345 (FIG. 24).

Figure 25:
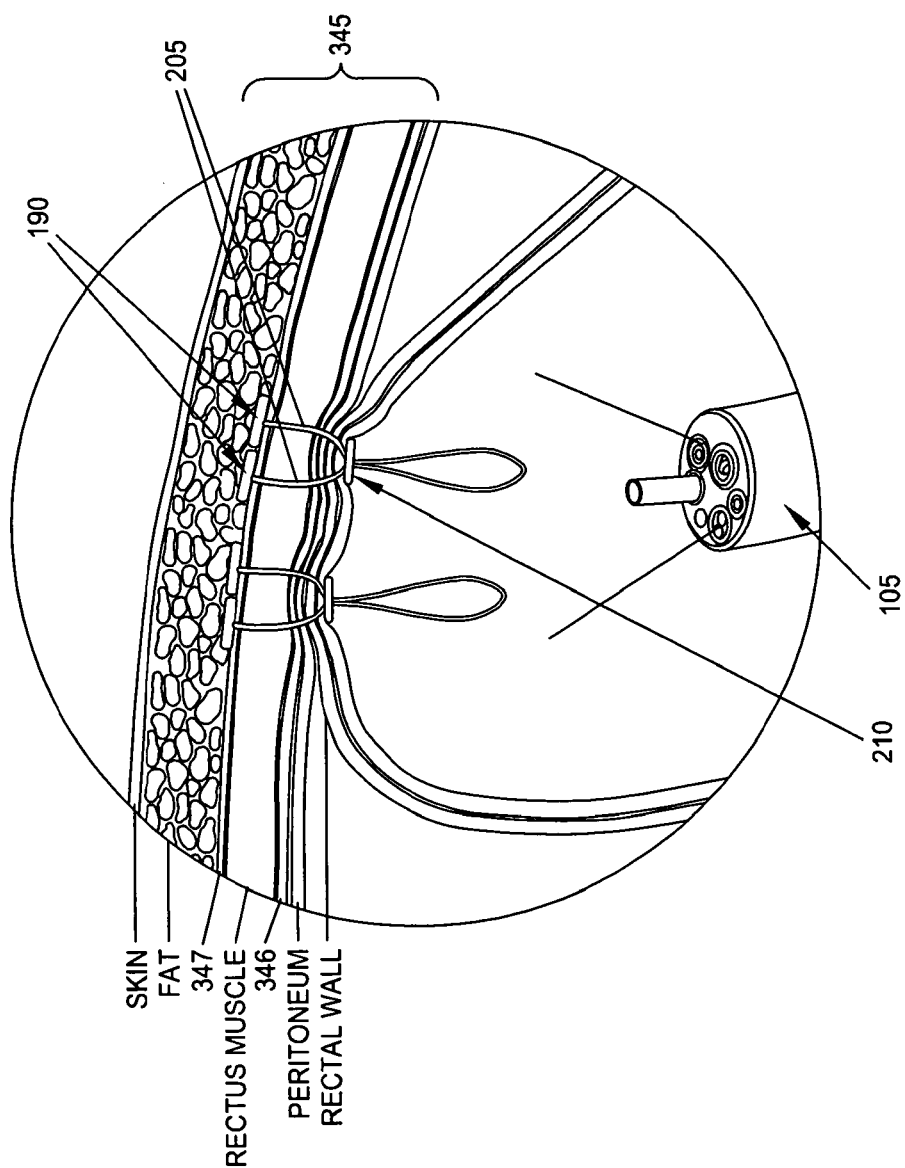
Figure 26:
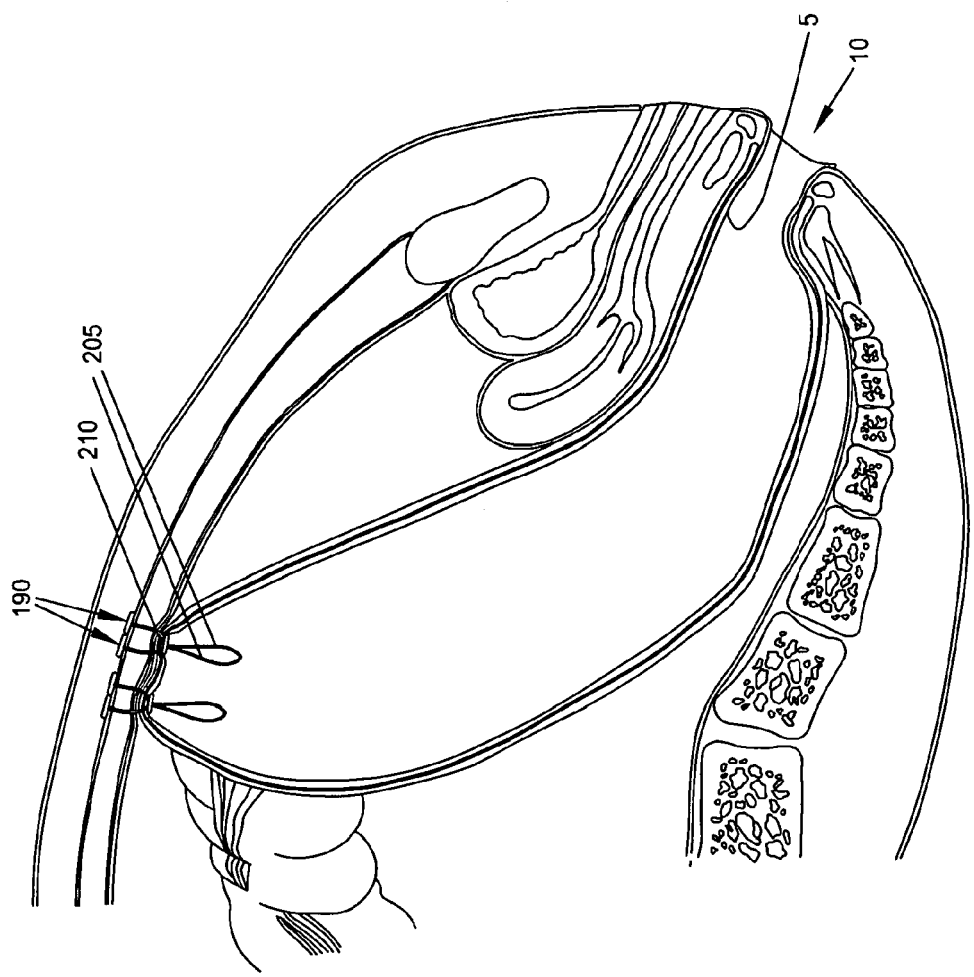

At this point, prolapse treatment instrument 305 and the tissue fixation device (e.g., fastener deployment device 115) may be used to make additional fixations of rectum 5 to supporting tissue (e.g., anterior abdominal wall 345), such as is shown in FIG. 25. Once rectum 5 has been properly fixed in place, the apparatus is withdrawn. See FIG. 26.

If desired, prolapse treatment instrument 305 can be slidably mounted to endoscope 105.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for treating rectal prolapse, the method comprising:
    inserting a rectum-gripping and advancement apparatus and a fastener deployment device into a prolapsed rectum via an anus;
    securely engaging the prolapsed rectum by maneuvering the rectum-gripping and advancement apparatus;
    advancing the rectum-gripping and advancement apparatus distally to return the prolapsed rectum to its normal, non-prolapsed state;
    while maintaining the rectum-gripping and advancement apparatus in position within the prolapsed rectum, using the fastener deployment device to advance a fastening device distally to a fastening site, and passing a portion of the fastening device through the wall of the prolapsed rectum at the fastening site, through a mesorectum and through a presacral fascia to fasten the prolapsed rectum to the presacral fascia, whereby to retain the prolapsed rectum in its normal, non-prolapsed state;
    wherein the rectum-gripping and advancement apparatus and the fastener deployment device are simultaneously slidably mounted directly to an endoscope via a distal mount.

2. A method according to claim 1 wherein the rectum-gripping and advancement apparatus comprises a shaft having a distal end comprising a tissue support for engaging an interior wall of the prolapsed rectum.

3. A method according to claim 2 wherein the tissue support comprises an opening.

4. A method according to claim 3 wherein the tissue support is generally circular in shape, with the opening located in a middle of the tissue support.

5. A method according to claim 3 wherein the step of securing the prolapsed rectum to the presacral fascia is performed through the opening in the tissue support.

6. A method according to claim 2 wherein an exterior of the tissue support includes texturing.

7. A method according to claim 6 wherein the texturing comprises a layer of at least one selected from the group consisting of suture, foam and fabric secured to the tissue support.

8. A method according to claim 2 wherein the shaft comprises a proximal end having a handle.

9. A method according to claim 2 wherein the step of securing the prolapsed rectum to the presacral fascia is performed around a periphery of the tissue support.

10. A method according to claim 1 wherein the method is performed under visualization provided by an endoscope.

11. A method according to claim 1 wherein the fastening device comprises at least one selected from the group consisting of a fastener and suture.

12. A method according to claim 11 wherein the fastener is selected from the group consisting of shaft-type tacks, legged staples, multi-part fasteners, and tacks comprising a body having a suture extending therefrom.

13. A method according to claim 11 wherein the fastener consists of at least one substantially rigid element having a suture attached thereto.

14. A method according to claim 11 wherein the fastener further comprises a securement band for securing the suture.

15. A method according to claim 1 wherein the prolapsed rectum is secured to the presacral fascia by suturing.

16. A method according to claim 1 wherein a securement location for securing the prolapsed rectum to the presacral fascia is determined by identifying an anatomical landmark.

17. A method according to claim 16 wherein the anatomical landmark is determined from a location within the prolapsed rectum.

18. A method according to claim 16 wherein the anatomical landmark is identified by an ultrasound probe disposed within the prolapsed rectum.

19. A method according to claim 16 wherein the anatomical landmark is identified by an endoscope disposed within the prolapsed rectum.

20. A method according to claim 16 wherein the anatomical landmark is the sacral promontory.

21. A method according to claim 1 wherein the prolapsed rectum is secured to the presacral fascia a plurality of fasteners.

* * * * *